(12) United States Patent
Kahlert et al.

(10) Patent No.: US 6,919,086 B1
(45) Date of Patent: Jul. 19, 2005

(54) GRAMINAE POLLEN ALLERGEN MUTANTS FOR SPECIFIC IMMUNOTHERAPY, AND PRODUCTION AND USE OF THE SAME

(75) Inventors: Helga Kahlert, Darmstadt (DE);
Hans-Thomas Stüwe, Darmstadt (DE);
Helmut Fiebig, Darmstadt (DE); Oliver Cromwell, Darmstadt (DE);
Wolf-Meinhard Becker, Darmstadt (DE); Albrecht Bufe, Darmstadt (DE);
Gabriele Schramm, Darmstadt (DE);
Lothar Jäger, Darmstadt (DE);
Wolf-Dieter Müller, Darmstadt (DE)

(73) Assignee: Merck Patent Gesellschaft mit, Darmstadt (DE)

( * ) Notice: Subject to any disclaimer, the term of this patent is extended or adjusted under 35 U.S.C. 154(b) by 0 days.

(21) Appl. No.: 09/381,903

(22) PCT Filed: Mar. 16, 1998

(86) PCT No.: PCT/EP98/01507

§ 371 (c)(1),
(2), (4) Date: Apr. 17, 2000

(87) PCT Pub. No.: WO98/43657

PCT Pub. Date: Oct. 8, 1998

(30) Foreign Application Priority Data

Mar. 27, 1997 (DE) .......................................... 197 13 001

(51) Int. Cl.[7] .............................................. A61K 39/36
(52) U.S. Cl. ................................ 424/275.1; 424/185.1; 530/379; 514/12
(58) Field of Search ...................... 424/275.1; 530/379, 530/350; 514/12

(56) References Cited

FOREIGN PATENT DOCUMENTS

| WO | 91 06571 | 5/1991 |
|----|----------|--------|
| WO | 94 04564 | 3/1994 |

OTHER PUBLICATIONS

Kuby et al., Immunology, 4th edition, 2000, Freeman, Publishers, New York, Table 16–1 and Figure 16–2 and p. 14.*

Mikayama et al. (PNAS, 1993, 90: 10056–10060).*

Ngo et al, in The Protein Folding Problem and Tertiary Structure Prediction, 1994. (ed.), Birkhauser, Boston, MA, pp. 433 and 492–495.*

Cao et al. (Allergy 1995 ; 50(suppl 25) : 37–44).*

Maasch et al. (Clin. Rev. Allergy, 1987; 5:89–106).*

Smith et al. (Molecular Immunolgy 1996; 33(4/5): 399–405).*

Vrtala et al. (J. Immunol, 1993; 151(9): 4773–4781).*

Bufe et al. (FEBS Letters 1995; 363: 6–12).*

Coleman et al. (Research in Immunology, 1994; 145(1): 33–36).*

Abaza et al (Journal of Protein Chemistry. vol. 11. No. 5. 1992. pp. 433–444).*

Lederman et al. (Molecular Immunology 28: 1171–1181, 1991).*

Li et al. (PNAS 77: 3211–3214, 1980).*

Muller W.D. et al.: "Group five allergens of timothy grass . . . "Int. Arch. Allergy Immunol., vol. 109, 1996 . pp. 353–355.

Becker, W.M.: "Molekulare charakterisierung von Allergenen" Immun. Infekt., vol 22, 1994 pp. 82–87.

* cited by examiner

*Primary Examiner*—Patrick J. Nolan
(74) *Attorney, Agent, or Firm*—Millen, White, Zelano & Branigan, P.C.

(57) ABSTRACT

The invention relates to modified recombinant allergen mutants which can be obtained from recombinant allergens which are derived from allergens which can be obtained by extraction from natural raw materials such as pollen of the species *Phleum pratense*. While these modified recombinant allergens stimulate lymphocytes from patients who are allergic to pollent to proliferate and synthesize cytokines, they exhibit a markedly diminished ability to bind to the IgE antibodies which are present in the serum of the T lymphocyte donors and to grass pollen allergen-specific IgEs and can therefore be used for a specific, made-to-release allergy therapy.

20 Claims, 6 Drawing Sheets

GRAMINAE POLLEN ALLERGEN MUTANTS FOR SPECIFIC IMMUNOTHERAPY, AND PRODUCTION AND USE OF THE SAME

CROSS-REFERENCE TO RELATED APPLICATIONS

This application claims benefit of PCT/EP98/01507, filed Mar. 16, 1998, under 35 U.S.C. §371.

The invention relates to modified recombinant allergens (mra) which are derived from allergens which can be obtained from natural raw materials by extraction. Pollen grains from *Gramineae,* such as *Phleum pratense, Lolium perenne, Dactylus glomerata, Poa pratensis, Cynodon dactylon* and *Holcus lanatus,* inter alia, are used as the natural raw material.

Extracts of *Gramineae* pollen, as employed for diagnostic and therapeutic use, consist of a heterogeneous mixture of proteins in glycoproteins, some of which react with IgE antibodies of allergic patients and are termed allergens by definition. The molecular properties of these allergens enable them to be classified into 6 groups, in association with which the cross-reactivity of the *Gramineae* species in question is relatively high. The dominant allergen groups (main allergens) are groups 5 and 1, in accordance with the customary allergen classification (Liebers et al., Clin. Exper. Allergy, 26, 494–516 (1996)). The N-terminal amino acid sequences and/or the partial or complete deduced amino acid sequences of groups 5 and 1 of the main allergens are known (Vrtala et al., J. Immunology 151, 4773–4781 (1993) and Bufe et al. FEBS. Lett. 263, 6–12 (1995)). Furthermore, methods for cloning these main allergens have been described (Scheiner et al. Int. Arch Allergy Immuno. 98, 93–96 (1992)).

At present, aqueous extracts of *Gramineae* pollen are used for the in-vitro diagnosis of type 1 allergies. These extracts are also the basis for in-vitro diagnosis and subsequent specific immunotherapy (Fiebig H., Allergo Journal 7, 377–382 (1995)). The use of native allergen extracts for specific immunotherapy is restricted by the IgE-dependent, allergic reactions (side reactions) which are induced under these circumstances. For this reason, native allergen extracts can only be administered in doses which are below the side effect threshold. In order to achieve the high allergen concentrations which are required for the therapeutic effect, the extracts are administered by means of several consecutive injections at a concentration which increases up to the maintenance dose. By means of adsorption onto gels, it is possible to use allergen extracts for hyposensitization in a manner which is more efficient and less subject to side effects.

A further improvement was achieved by chemically modifying the allergens to form allergoids, which have a lower reactivity with IgE but which to a large extent retain their immunogenecity (Fiebig H., Allergo Journal 7, 377–382 (1995) and Maasch et al. Clin. Ref. Allergy 5, 89–106 (1987)).

In initial investigations with house dust mite allergens, there are indications that a reduction in the IgE reactivity can be achieved by means of directed amino acid replacement (Smith et al. Mol. Immunol. 33, 339–405 (1996) and Nishiyama et al. Mol. Immunol. 32, 1021–1029 (1995)).

At the moment, the established hyposensitization of patients who are allergic to *Gramineae* pollen is carried out using natural extracts which comprise all the known allergens and also non-allergenic but immunogenic minor components in substantial concentrations, although, for allergen-specific therapy, only those allergen molecules against which the particular patient is in fact sensitized are required. This means that the allergic patient is unavoidably treated with components which do not contribute to his hyposensitization and which can induce side effects.

As a result of the availability of modified recombinant allergens, individual allergens, or defined mixtures, can be used as pharmaceuticals for the hyposensitization in accordance with the individual sensitization spectrum.

This provides the possibility of a specific, made-to-measure therapy.

The invention was based on the object of discovering novel compounds having valuable properties, in particular compounds which can be used for producing pharmaceuticals.

It has been found that the compounds of the present invention, in the form of the modified recombinant allergens and their salts and solvates, possess very valuable pharmacological properties while at the same time being well tolerated. In particular, they have a hyposensitizing effect.

The compounds can be used as pharmaceutical active compounds in human and veterinary medicine, in particular for therapy in association with allergic diseases and for hyposensitizing allergic patients.

Surprisingly, success has been achieved, within the context of the present invention, in using recombinant allergens, whose amino acid sequences are identical to those of allergen molecules which occur in natural extracts, to construct mutants, by means of genetic manipulation methods which are known per se, which react specifically with T lymphocytes of patients who are allergic to grass pollen, i.e. which stimulate the T lymphocytes to proliferate and synthesize cytokines or which induce anergy in the T lymphocytes, but which exhibit a markedly diminished ability to bind to the IgE antibodies which are present in the serum of the T lymphocyte donors and to grass pollen allergen-specific IgE from the sera of other patients who are allergic to grass pollen.

This effect, which is not seen either in the case of the naturally occurring allergens or in the case of the recombinant allergens, is desirable because the IgE-mediated side effects which otherwise occur during hyposensitization are avoided or are at least strongly diminished, it ensures recognition of the modified recombinant allergens by the TH memory lymphocytes of the allergic patients, it creates the conditions for normalizing the balance, which is distributed in the allergic patient, of the variously differentiated TH subpopulations, it makes possible a therapeutic effect by means of anergizing and/or eliminating the allergen-reactive T cells and functionally reorienting a specific T cell population which is TH2-dominated to one which is TH0/TH1-aligned, the immunoglobulin synthesis can be switched from the formation of spec. IgE antibodies (TH2-controlled), which is typical for the allergic patient, to the preferred synthesis of IgG antibodies (TH1-controlled), and, as a result, the condition of the patients can be expected to be markedly improved when they are treated with the novel, modified recombinant allergens.

The invention relates to modified recombinant allergens which are derived from allergens which are obtained from natural raw materials by extraction. Pollen grains from Gramineae, such as *Phleum pratense, Lolium perenne, Dactylus glomerata, Poa pratensis, Cynodon dactylon* and *Holcus lanatus*, inter alia, are used as the natural raw material. In particular, the invention relates to modified recombinant allergens which are derived from the main allergens of groups 1–6 and whose reactivity with the IgE antibodies of patients who are allergic to grass pollen is eliminated or at least reduced while that with the T lymphocytes is still retained. The modified recombinant allergens differ from the wild type in that the genes for the allergens have been modified by genetic manipulation methods such that the polypeptides which they encode exhibit substitutions, deletions and/or additions of individual or several amino acids as compared with the wild type. At the same time, the dominant T cell-reactive regions of the modified recombinant allergens (T cell epitopes) are not altered by genetic manipulation.

Preferably, the modified recombinant allergens are derived from the main allergens of group 5 or else of group 1. In particular, the novel allergens are derived from the main Phl p 5b allergen.

Using the single-letter code for amino acids, the sequence of Phl p 5b is as follows:

```
ADAGYAPATPAAAGAAAGKATTEEQKLIEDINVGFKAAVAAAASVPAADK
1        10        20        30        40        50
FKTFEAAFTSSSKAAAAKAPGLVPKLDAAYSVAYKAAVGATPEAKFDSFV
51       60        70        80        90        100
ASLTEALRVIAGALEVHAVKPVTEEPGMAKIFAGELQIIDKIDAAFKVAA
101      110       120       130   140         150
TAAATAPADDKFTVFEAAFNKAIKESTGGAYDTYKCIPSLEAAVKQAYAA
151      160       170       180   190         200
TVAAAPQVKYAVFEAALTKAITAMSEVQKVSQPATGAATVAAGAATTAAG
201      210       220       230       240       250
AASGAATVAAGGYKV (SEQ ID NO 87)
251      260 265
```

The invention particularly relates to modified recombinant allergens in which at least one, or a combination, of the regions 16–42, 135–149 and 180–206 of the Phl p 5b polypeptide, consisting of a total of 265 amino acids, is/are not altered. The segments to be preserved are the T cell epitope regions.

The said amino acid residues can also be derivatized. Modifications of the side chains are particularly appropriate in this context.

The amino acid residue abbreviations which are listed above and below stand for the residues of the following amino acids:

Ala=A alanine
Asn=N asparagine
Asp=D aspartic acid
Arg=R arginine
Cys=C cysteine
Gln=Q glutamine
Glu=E glutamic acid
Gly=G glycine
His=H histindine
Ile=I isoleucine
Leu=L leucine
Lys=K lysine
Met=M methionine
Phe=F phenylalanine
Pro=P proline
Ser=S serine
Thr=T threonine
Trp=W tryptophan
Tyr=Y tyrosine
Val=V valine.

In addition, the abbreviations below have the following meanings:

Ac acetyl
BOC tert-butoxycarbonyl
CBZ or Z benzyloxycarbonyl
DCCI dicyclohexylcarbodiimide
DMF dimethylformamide
EDCI N-ethyl-N,N'-(dimethylaminopropyl)carbodiimide
Et ethyl
FCA fluoresceincarboxylic acid
FITC fluorescein isothiocyanate
Fmoc 9-fluorenylmethoxycarbonyl
HOBt 1-hydroxybenzotriazole
Me methyl
MBHA 4-methylbenzhydrylamine
Mtr 4-methoxy-2,3,6-trimethylphenylsulfonyl
HONSu N-hydroxysuccinimide
OBut tert-butyl ester
Oct octanoyl
OMe methyl ester
OEt ethyl ester
POA phenoxyacetyl
Sal salicyloyl
TFA trifluoroacetic acid
Trt trityl (triphenylmethyl).

Insofar as the abovementioned amino acids are able to occur in several enantiomeric forms, all these forms, and also their mixtures (e.g. the DL forms), are included both in that which is stated above and in that which follows. Furthermore, the amino acids can, for example as constituents of compounds, be provided with appropriate protecting groups which are known per se.

So-called prodrug derivatives, i.e. compounds which are modified with, for example, alkyl or acyl groups, sugars or oligopeptides and which are rapidly cleaved in the organism to form the active novel compounds, are also included in the novel compounds.

These prodrugs also include biodegradable polymer derivatives of the novel compound as described, for example, in Int. J. Pharm. 115, 61–67 (1995).

The novel allergens may possess one or more chiral centres and therefore occur in different stereoisomeric forms. The present invention encompasses all these forms.

Very particular preference is given to modified recombinant allergens which are derived from the following group of polypeptides, which are derived from Phl p 5b:

PM1 ($N^{32} \to D$, $D^{49} \to L$, $K^{50} \to A$)
PM2 ($D^{49} \to L$, $K^{50} \to A$)
PM3 ($A^{13} \to C$)
DM1 ($\Delta K^{50} \to P^{\Delta 132}$, $D^{49} \to L$)
DM 2 ($\Delta F^{51} - G^{178}$, $D^{49} - L$, $K^{50} - A$)
DM2* ($\Delta F^{51} - G^{178}$, 179–217 altered sequence)
DM3 ($\Delta A^{154} - T^{177}$, $A^{220} \to T$)

In the above sequences, the amino acids or amino acid sequences which are modified are indicated in each case.

In the context, PM1 denotes point mutation 1 and has the following sequence (the amino acids which are replaced as compared with Phl p 5b are printed in bold):

```
ADAGYAPATPAAAGAAAGKATTEEQKLIEDIDVGFKAAVAAAASVPAALA
1        10        20        30        40        50
FKTFEAAFTSSSKAAAAKAPGLVPKLDAAYSVAYKAAVGATPEAKFDSFV
51       60        70        80        90       100
ASLTEALRVIAGALEVHAVKPVTEEPGMAKIPAGELQIIDKIDAAFKVAA
101      110       120       130  140            150
TAAATAPADDKFTVFEAAFNKAIKESTGGAYDTYKCIPSLEAAVKQAYAA
151      160       170       180       190       200
TVAAAPQVKYAVFEAALTKAITAMSEVQKVSQPATGAATVAAGAATTAAG
201      210       220       230       240       250
AASGAATVAAGGYKV          (SEQ ID NO 88)
251      260  265
```

The other particularly preferred peptides have the following sequences:

```
PM2 (D43 → L, K50 → A):
ADAGYAPATPAAAGAAAGKATTEEQKLIEDINVGFKAAVAAAASVPAALA            (SEQ ID NO 89)
1        10        20        30        40        50
FKTFEAAFTSSSKAAAAKAPGLVPKLDAAYSVAYKAAVGATPEAKFDSFV
51       60        70        80        90       100
ASLTEALRVIAGALEVHAVKPVTEEPGMAKIPAGELQIIDKIDAAFKVAA
101      110       120       130  140            150
TAAATAPADDKFTVFEAAFNKAIKESTGGAYDTYKCIPSLEAAVKQAYAA
151      160       170       180       190       200
TVAAAPQVKYAVFEAALTKAITAMSEVQKVSQPATGAATVAAGAATTAAG
201      210       220       230       240       250
AASGAATVAAGGYKV
251      260  265
PM3 (A13 → C):
ADAGYAPATPAACGAAAGKATTEEQKLIEDINVGFKAAVAAAASVPAADK            (SEQ ID NO 90)
1        10        20        30        40        50
FKTFEAAFTSSSKAAAAKAPGLVPKLDAAYSVAYKAAVGATPEAKFDSFV
51       60        70        80        90       100
ASLTEALRVIAGALEHAVKPVTEEPGMAKIPAGELQIIDKIDAAFKVAA
101      110       120       130  140            150
TAAATAPADDKFTVFEAAFNKAIKESTGGAYDTYKCIPSLEAAVKQAYAA
151      160       170       180       190       200
TVAAAPQVKYAVFEAALTKAITAMSEVQKVSQPATGAATVAAGAATTAAG
201      210       220       230       240       250
AASGAATVAAGGYKV
251      260  265
DML (Δ K60 → PΔ111, D49 → L):
ADAGYAPATPAAAGAAAGKATTEEQKLIEDINVGFKAAVAAAASVPAALA            (SEQ ID NO 91)
1        10        20        30        40        50
GELQIIDKIDAAFKVAATAAATAPADDKFTVFEAAFNKAIKESTGGAYDTYK
51       60        70        80        90       100
CIPSLEAAVKQAYAATVAAAPQVKYAVFEAALTKAITAMSEVQKVSQPATG
103      110       120       130       140       150
AATVAAGAATTAAGAASGAATVAAGGYKV
154      160       170       180
DM 2 (Δ F61 - G178, D49 - L, K50 - A):
ADAGYAPATPAAAGAAAGKATTEEQKLIEDINVGFKAAVAAAASVPAALA            (SEQ ID NO 92)
1        10        20        30        40        50
GAYDTYKCIPSLEAAVKQAYAATVAAAPQVKYAVFEAALTKAITAMSEVQK
51       60        70        80        90       100
VSQPATGAATVAAGAATTAAGAASGAATVAAGGYKV
102      110       120       130  137
```

This sequence corresponds to that of DM2 where, however, the amino acids of positions 179–217 of the starting peptide Phl p 5b additionally exhibit an altered sequence and all the subsequent amino acids are missing.

```
DM3 (Δ A254 - T177 , A120 → T):
ADAGYAPATPAAAGAAAGKATTEEQKLIEDINVGFKAAVAAAASVPAADK
1        10        20        30        40        50
FKTFEAAFTSSSKAAAAKAPGLVPKLDAAYSVAYKAAVGATPEAKFDSFV
51       60        70        80        90       100
ASLTEALRVIAGALEVHAVKPVTEEPGMAKIPAGELQIIDKIDAAFKVAA
101      110       120       130  140            150
TAAGGAYDTYKCIPSLEAAVKQAYAATVAAAPQVKYAVFEAALTKTITAMS
151      160       170       180       190       200
EVQKVSQPATGAATVAAGAATTAAGAASGAATVAAGGYKV
202      210       220       230       240
(SEQ ID NO 93)
```

The invention furthermore relates to a process for preparing modified recombinant allergens by using the polymerase chain reaction and/or its variants. When the peptide sequence is known, the allergens can also be prepared by means of methods of peptide synthesis which are known per se, e.g. the modified Merrifield technique, as described in the literature (e.g. in the standard works such as Houben-Weyl), Methoden der organischen Chemie (Methods of Organic Chemistry), Georg-Thieme-Verlag, Stuttgart;), under reaction conditions which are known and are suitable for the said reactions. In this context, use can also be made of variants which are known per se but which are not mentioned here in detail. It is furthermore possible to liberate the peptides from one of their functional derivatives by treating the latter with a solvolyzing or hydrogenolyzing agent, and/or convert a basic or acidic peptide into none of its salts or solvates by treating it with an acid or base.

Preferred starting compounds for the solvolysis or hydrogenolysis are those which, in place of one or more free amino and/or hydroxyl groups contain corresponding protected amino and/or hydroxyl groups, preferably those which, in place of an H atom which is connected to an N atom, carry an amino protecting group, e.g. those which, in place of an NH$_2$ group, contain an NHR' group (in which R' is an amino protecting group, e.g. BOC or CBZ).

Starting compounds are also preferred which, in place of the H atom of a hydroxyl group, carry a hydroxyl protecting group, e.g. those which, in place of a hydroxyphenyl group, contain an R"O-phenyl group (in which R" is a hydroxyl protecting group).

Several—identical or different—protected amino groups and/or hydroxyl groups may also be present in the molecule of the starting compound. If the protecting groups which are present are different from each other, they can in many cases be eliminated selectively.

The expression "amino protecting group" is known generally and refers to groups which are suitable for protecting (blocking) an amino group from chemical reactions but which can be removed readily after the desired chemical reaction has been carried out at other sites of the molecule. Typical groups of this nature are, in particular, unsubstituted or substituted acyl, aryl, aralkoxymethyl or aralkyl groups. Since the amino protecting groups are removed after the desired reaction (or reaction sequence) has taken place, their nature and size is otherwise not critical; however, those amino protecting groups are preferred which have 1–20, in particular 1–8, C atoms. In connection with the present process the expression "acyl group" is to be interperted in the widest possible sense. It encompasses acyl groups which are derived from aliphatic, aralipathic, aromatic or heterocyclic carboxylic acids or sulfonic acids, and, in particular, alkoxycarbonyl, aryloxycarbonyl and, especially, aralkoxycarbonyl groups. Examples of acyl groups of this nature are alkanoyl, such as acetyl, propionyl or butyryl; aralkanoyl, such as phenylacetyl; aroyl, such as benzoyl or toluoyl; aryloxyalkanoyl, such as POA; alkoxycarbonyl, such as methoxycarbonyl, ethoxycarbonyl, 2,2,2-trichloroethoxycarbonyl, BOC or 2-iodoethoxycarbonyl; aralkyloxycarbonyl, such as CBZ ("carbobenzoxy"), 4-methoxybenzyloxycarbonyl or FMOC; arylsulfonyl, such as Mtr. Preferred amino protecting groups are BOC and Mtr, and also CBZ, Fmoc, benzyl and acetyl.

The expression "hydroxyl protecting group" is likewise known generally and refers to groups which are suitable for protecting a hydroxyl group from chemical reactions but which can readily be removed after the desired chemical reaction has been carried out at other sites of the molecule. Typical groups of this nature are the abovementioned unsubstituted or substituted aryl, aralkyl or acyl groups and also alkyl groups. The nature and size of the hydroxyl protecting groups is not critical since they are removed once again after the desired chemical reaction or reaction sequence has taken place; groups having 1–20, in particular 1–10, C atoms are preferred. Examples of hydroxyl protecting groups are, interalia, benzyl, p-nitrobenzoyl, p-toluenesulfonyl, tert-butyl and acetyl, with benzyl and tert-butyl being particularly preferred. The COOH groups in aspartic acid and glutamic acid are preferably protected in the form of their tert-butyl esters (e.g. Asp (OBut)).

Depending on the protecting group employed, the compounds are liberated from their functional derivatives using, for example, strong acids, expediently using TFA or perchloric acid, but also using other strong inorganic acids, such as hydrochloric acid or sulfuric acid, strong organic carboxylic acids, such as trichloroacetic acid, or sulfonic acids, such as benzenesulfonic acid or p-toluenesulfonic acid. It is possible, but not always necessary, for a supplementary inert solvent to be present. Preferred suitable inert solvents are organic, for example carboxylic, acids, such as acetic acid, ethers, such as tetrahydrofuran or dioxane, amides, such as DMF, halogenated hydrocarbons, such as dichloromethane, and, in addition, also alcohols, such as methanol, ethanol or isopropanol, and water. Mixtures of the abovementioned solvents are also suitable. TFA is preferably used in excess without the addition of another solvent; perchloric acid is used in the form of a mixture consisting of acetic acid and 70% perchloric acid in a ratio of 9:1. The reaction temperatures for the cleavage are expediently between about 0° and 50°; the reaction is preferably carried out between 15 and 30° or room temperature.

The BOC, OBut and Mtr groups can, for example, be preferably eliminated using TFA in dichloromethane or using approximately 3 to 5N HCl in dioxane at 15–30°; the FMOC group can be eliminated using an approximately 5 to 50% solution of dimethylamine, diethylamine or piperadine in DMF at 15–30°.

The trityl group is employed for protecting the amino acids histidine, asparagine, glutamine and cysteine. Depending on the desired end product, it is eliminated using TFA/10% thiophenol, with the trityl group being eliminated from all the amino acids mentioned, or using TFA/anisole or TFA/thioanisole, in which case the trityl group is only eliminated from His, Asn and Gln and remains on the Cys side chain.

Protecting groups which can be removed hydrogenolytically (e.g. CBZ or benzyl) can be eliminated, for example, by treatment with hydrogen in the presence of a catalyst (e.g. a precious metal catalyst such as palladium, expediently on a support such as carbon). Suitable solvents in this context are the abovementioned solvents, in particular, for example, alcohols, such as methanol or ethanol, or amides, such as DMF. As a rule, the hydrogenolysis is carried out at temperatures of between about 0 and 100° and under pressures of between about 1 and 200 bar, preferably at 20–30° and under 1–10 bar. Hydrogenolysis of the BZ group is, for example, effected satisfactorily on 5 to 10% Pd/C in methanol or using ammonium formate (instead of hydrogen) on Pd/C in methanol/DMF at 20–30°.

An acid can be used to convert a base into the affiliated acid addition salt, for example by reacting equivalent quantities of the base and the acid in an inert solvent, such as ethanol, and then concentrating by evaporation. Acids which yield physiologically harmless salts are particularly suitable for this reaction. Thus, use can be made of inorganic acids, for example sulfuric acid, nitric acid, hydrohalic acids, such as hydrochloric acid or hydrobromic acid, phosphoric acids, such as orthophosphoric acid, or sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid. Salts with acids which are not physiologically harmless, eg. picrates, may be used for isolating and/or purifying compounds of the formula I.

On the other hand, an acid of the formula I can be converted into one of its physiologically harmless metal or ammonium salts by reacting it with a base. In this context, suitable salts are, in particular, the sodium, potassium, magnesium, calcium and ammonium salts, and also substituted ammonium salts, e.g. the dimethyl-, monoethyl-, diethyl- or diisopropyl-ammonium salts, cyclohexyl, or dicyclohexyl-ammonium salts, or dibenzylethylenediammonium salts, and, furthermore, salts with arginine or lysine, for example.

The following steps are necessary for ascertaining the DNA or amino acid sequences:

The allergenic constituents of the extracts, which have been prepared by means of customary methods, are identified and their important physiocochemical parameters are characterized. Constituents are identified as being allergens by demonstrating their ability to bind to the IgE antibodies of allergic patients. As a rule, this is done using methods which are known per se, such as SDS-PAGE, isoelectrofocusing and then Western blotting with sera from allergic patients, with only the binding antibodies of the IgE isotype being developed. In this context, care has to be taken to ensure that an adequately large number of types of clinically verified allergic patients (a value of 20 should be set as being the lowest number) are used. Other methods, such as CIE or CRIE, can also be used as alternatives.

These *Gramineae* pollen allergens which have been identified and characterized in this way can be prepared analytically such that it is possible to carry out an N-terminal amino acid determination. Furthermore, the allergens can also be purified biochemically and used for preparing monoclonal antibodies. These monoclonal antibodies can, like the IgE antibodies in the sera of allergic patients, be used for the immunological identification and characterization of the allergens from natural sources or of the molecules which are prepared by the recombinant technique.

On the basis of this information on allergens and the means for identifying them, it is possible to clone the allergens using known genetic manipulation methods and to express them as recombinant allergens. The DNA clones of the recombinant allergens which have been isolated and characterized using customary methods are the basis for the modifications which are carried out by means of genetic manipulation and which give rise to the novel, modified recombinantly prepared allergen molecules.

In order to ensure the reactivity of the novel, modified recombinant allergens, it is also necessary to identify the T cell epitopes.

The basis for this is knowledge of the amino acid sequence of the allergen in question or of the corresponding, underlying DNA sequence. As a rule, the amino acid sequence is deduced from the DNA sequence of the recombinant allergens. Consequently, within the context of this invention, the affiliated DNA sequences for every peptide sequence cited are also included, even when these DNA sequences are not explicitly disclosed since they can be derived from the peptide sequences in a known and simple manner.

Based on the amino acid sequence, a series of overlapping oligopeptides is prepared by means of customary methods, such as solid phase synthesis using modified Merrifield techniques, with the entire sequence of the allergens being covered. Oligopeptides having in each case 6–20, preferably 9–15, amino acid residues may suitably be prepared in this context. Dodecapeptides which are offset by in each case 3 amino acids and which cover the entire sequence of the respective allergen in an overlapping manner are very particularly suitable.

In order to identify the T cell epitopes, T cell clones from patients who are allergic to *Gramineae* pollen are established by repeated stimulation with the purified, natural or recombinantly prepared allergen in question using the customary method (Lit). For this, it is necessary to establish a representative number of T cell clones which derive from a sufficiently large number of donors.

These T cell clones are incubated with the above-described overlapping peptides and the ability of the latter to stimulate the T cells to proliferate is tested. The proliferation is determined by incorporating [$^3$H]-thymidine by means of methods which are customary per se. Those oligopeptides which induce adequate proliferation of the T cell clones are then regarded as peptide ligands which correspond to the T cell epitopes. The T cell epitopes which have been determined in this manner are used to define T cell-reactive regions of the allergens which, for their part, constitute the basis for constructing the novel modified recombinant allergens.

In order to ensure that modified recombinant allergens react with the T lymphocytes which are found in allergic patients, the primary structures of the T-cell-reactive regions which encompass the immunodominant T cell epitopes are partially or completely excluded from alterations.

Genetic manipulation is used to perform mutations in the DNA sequence underlying the remaining regions of the polypeptides (allergens) in order to process an altered primary structure. This altered primary structure destroys or limits the ability of sequence-dependent continuous B cell epitopes to bind to the IgE antibodies and, due to the formation of a modified tertiary structure as a consequence of the primary modification, completely or partially abolishes the ability of conformation-dependent, possibly discontinuous epitopes to react with their antibodies.

The mutations can be replacements of individual or several amino acids outside the T cell-reactive regions. Such point mutations are introduced into the DNA, which, for example, encodes rPhl p 5b, by means of site-specific mutagenesis using the polymerase chain reaction (PCR). The plasmid pGS13, an expression vector (pMalc) which contacts the cDNA for rPhl p 5b, can be used as the template in this context. Gene-specific primers which contain appropriate base replacements and also a new restriction site (Nhe I or Sph I) are used for the PCR. The fragments which are amplified in the PCR and which carry the mutation are ligated one after the other into a cloning vector and the complete product is then recloned into the pMalc expression vector.

Furthermore, mutations can be performed by means of differentially arranged deletions. In order to prepare the deletion mutants, truncated 3'-terminal fragments of the cDNA of rPHl p 5b are prepared in a PCR using gene-specific primers. Relatively large 3'-terminal fragments are removed from the starting vectors (pGS12 or pGS13) by means of restriction at internal cleavage sites and the fragments which were amplified in the PCR, and which are in each case smaller, are ligated in to replace them.

In an analogous manner, mutations involving additions of one or more amino acids can be produced by inserting additional DNA fragments.

The DNA clones which have been mutated by means of genetic manipulation and which encode modified recombinant allergens are recloned into suitable expression vectors and expressed in suitable host organisms. The fusion proteins are purified in a customary manner from the supernatants or disruptions of these host organisms and, after the fusion moiety has been eliminated, the modified recombinant allergens are prepared in the pure state using customary biochemical methods. It is important that the modified recombinant allergens be used for further tests as pure components which correspond to the natural allergens.

The effects of the induced mutations on the allergenicity, i.e. the ability to bind to the IgE antibodies of allergic patients, of the modified recombinant allergens is determined qualitatively and quantitatively by means of the EAST inhibition test. This assay shows whether a substance to be tested (modified recombinant allergen) is identical to, or different from, the natural allergen and/or the recombinant wild type. The extent of the immunochemical relatedness (cross reactivity) can also be quantified. This EAST inhibition test only takes the reaction with IgE antibodies into account.

Those modified recombinant allergen variants which exhibit an inhibitory effect, measured as $P_{rel}$ at 50% inhibition, which is decreased at least by a factor of $10^2$ as compared with the natural allergen and/or recombinant wild type are selected as being suitable.

The modified recombinant allergen variants which have been selected in this way are checked to see whether their T cell reactivity has in fact been retained. For this, a set of T cell clones which react with epitopes in the T cell-reactive regions are taken for testing in the first phase.

Only those modified recombinant allergens which stimulate the selected clones to proliferate are taken into consideration.

In the second phase, oligoclonal T cell lines, which have been established by repeated stimulation with the relevant allergens, are employed for the testing. Once again, only those modified recombinant allergens which at least give rise to a stimulation index (SI) of 50% of the SI of the wild type are taken into consideration.

In the third phase, polyclonal short-term T cell cultures from the peripheral blood of allergic patients are employed for testing.

Apart from the binding of the allergen to the spec. IgE, the allergen-induced, IgE-mediated release of histamine by allergic effect or cells is of pathophysiological importance for the allergic reaction (side effect). The reactivity of the effector cells (basophils and mast cells) and the epitope specificity of the IgE antibodies which are bound by way of FcεRI are also of importance in this context. For this reason, the modified recombinant allergen variants are tested for their ability to induce histamine release by the degranulation of IgE-loaded basophils which are isolated from the blood of allergic patients. In this functional test, the modified recombinant allergen variants which have been selected in accordance with the above selection regime have to exhibit a markedly reduced ability to release histamine.

The modified recombinant allergens which meet these requirements ensure reactivity with the majority of the TH cells which have a regulatory effect and, due to their diminished IgE reactivity, possess the requisite properties for being employed as therapeutic agents for the allergen-specific immunotherapy (hyposensitization) of patients who are allergic to *Gramineae* pollen.

The invention furthermore relates to pharmaceutical preparations which comprise one or more modified recombinant allergen(s) according to the present invention, and/or one of their physiologically harmless salts or solvates, and also, where appropriate, additional active compounds and/or auxiliary substances, for treating IgE-mediated allergies.

The invention furthermore relates to a process for producing pharmaceutical preparations, with at least one modified recombinant allergen and/or one of its physiologically harmless salts or solvates being brought into a suitable dosage from together with at least one solid, liquid or semiliquid carrier substance or auxiliary substance.

The invention furthermore relates to the use of the modified recombinant allergens and/or their physiologically harmless salts or solvates for producing pharmaceutical preparations, in particular by a non-chemical route. In this context, they can be brought into a suitable dosage form together with at least one solid, liquid and/or semiliquid carrier substance or auxiliary substance and, where appropriate, in combination with one or more additional active component(s). The pharmaceuticals are used for immunospecific therapy, i.e. for hyposensitization in association with allergies. It is likewise possible to conceive of using the modified recombinant allergens directly for the immunospecific therapy (hyposensitization) of allergies.

These preparations can be used in human or veterinary medicine as pharmaceuticals. Suitable carrier substances are organic or inorganic substances which are suitable for enteral (e.g. oral), parenteral or topical administration or for administration in the form of an inhalation spray and which do not react with the novel compounds, for example water, vegetable oils, benzyl alcohols, alkylene glycols, polyethylene glycols, glycerol triacetate, gelatin, carbohydrates, such as lactose and starch, magnesium stearate, talc or yellow soft paraffin. Tablets, pills, coated tablets, capsules powders, granules, syrups, juices or drops are, in particular, employed for oral use, while suppositories are employed for rectal use, solutions, preferably oily or aqueous solutions and, in addition, suspensions, emulsions or implants are employed for parentreal use, and ointments, creams or powders are employed for topical use. The novel compounds can also be lyophilized and the resulting lyophilates can, for example, be used to produce preparations for injection. The cited preparations can be sterilized and/or comprise auxiliary substances, such as lubricants, preservatives, stabilizers and/or wetting agents, emulsifiers, salts for affecting the osmotic pressure, buffering substances, dyes, flavourants and/or several additional active compounds, e.g. one or more vitamins. For administration as an inhalation spray, use can be made of sprays which comprise the active compound either dissolved or suspended in a propellant gas or propellant gas mixture (e.g. $CO_2$ or fluorochlorohydrocarbons). Expediently, the active compound is used in this context in micronized form, with it being possible for one or more additional, physiologically tolerated solvent(s), e.g. ethanol, to be present. Inhalation solutions can be administered using customary inhalers.

The compounds and their physiologically harmless salts, can be used for hyposensitizing allergic patients in association with controlling allergic diseases, in particular allergies which are provoked by grasses and grass pollen.

In this context, the novel substances can, as a rule, be administered in analogy with other known, commercially available peptides, in particular, however, in analogy with the compounds which are discussed in U.S. Pat. No. 4,472, 305, are preferably administered in doses of between about 0.05 and 500 mg, in particular of between 0.5 and 100 mg, per dosage unit. The daily dose is preferably between about 0.01 and 2 mg/kg of bodyweight. However, the special dose for each patient depends on a very wide variety of factors, for example on the efficacy of the special compound employed, on the age, bodyweight, general state of health and sex of the patient, on the diet, on the time and route of administration, on the rate of excretion, on the medicinal combination and on the severity of the particular disease to which the therapy applies. Parenteral administration is preferred.

In that which has been stated above, and in that which follows, all temperatures are given in ° C. In order to isolate the products, water is added, if necessary, and the mixture is adjusted, if necessary, depending on the constitution of the end product, to pH values of between 2 and 10 and extracted with ethyl acetate or dichloromethane; the phases are separated and the organic phase is dried over sodium sulfate and concentrated by evaporation; the residue is then purified by chromatography on silica gel and/or by means of crystallization.

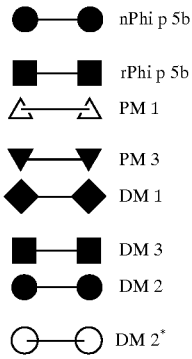

Figure 2:
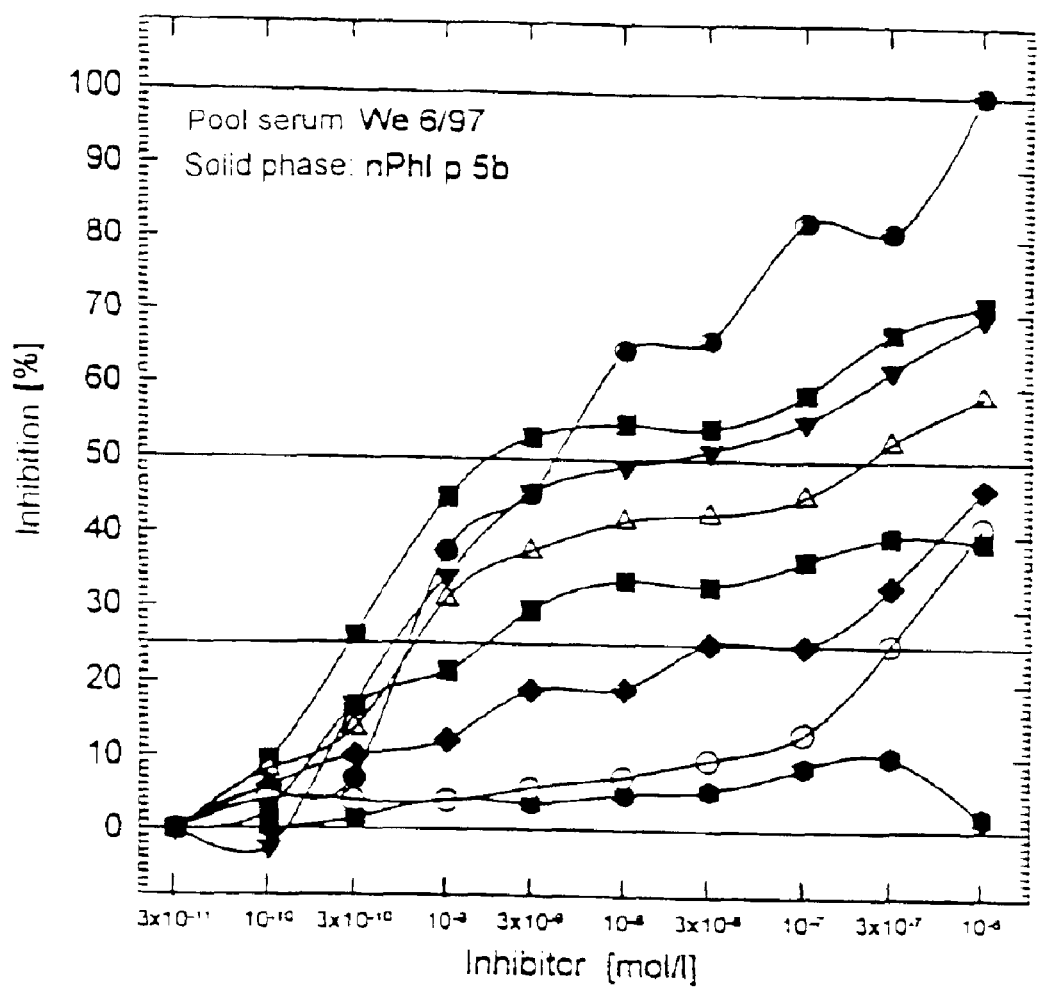

FIG. 2 shows EAST inhibition curves of the Phl p5b mutants using the allergic patient serum pool We 6.97. The inhibitors are:

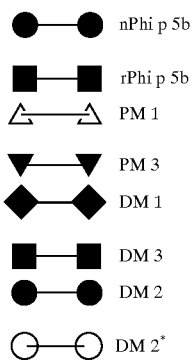

Figure 3:
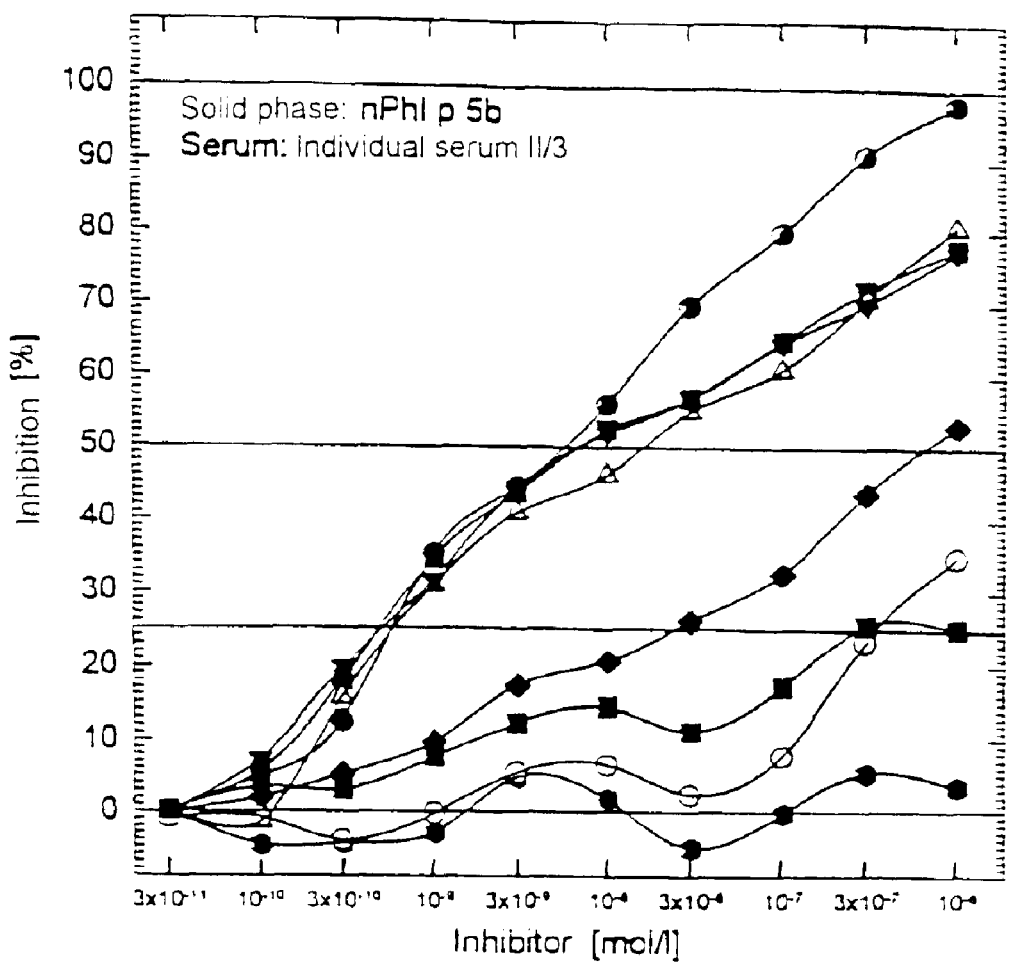

FIG. 3 shows EAST inhibition curves of the Phl p 5b mutants using the allergic patient serum pool 11/3.

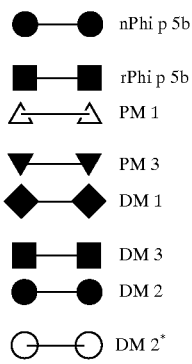

Figure 4:
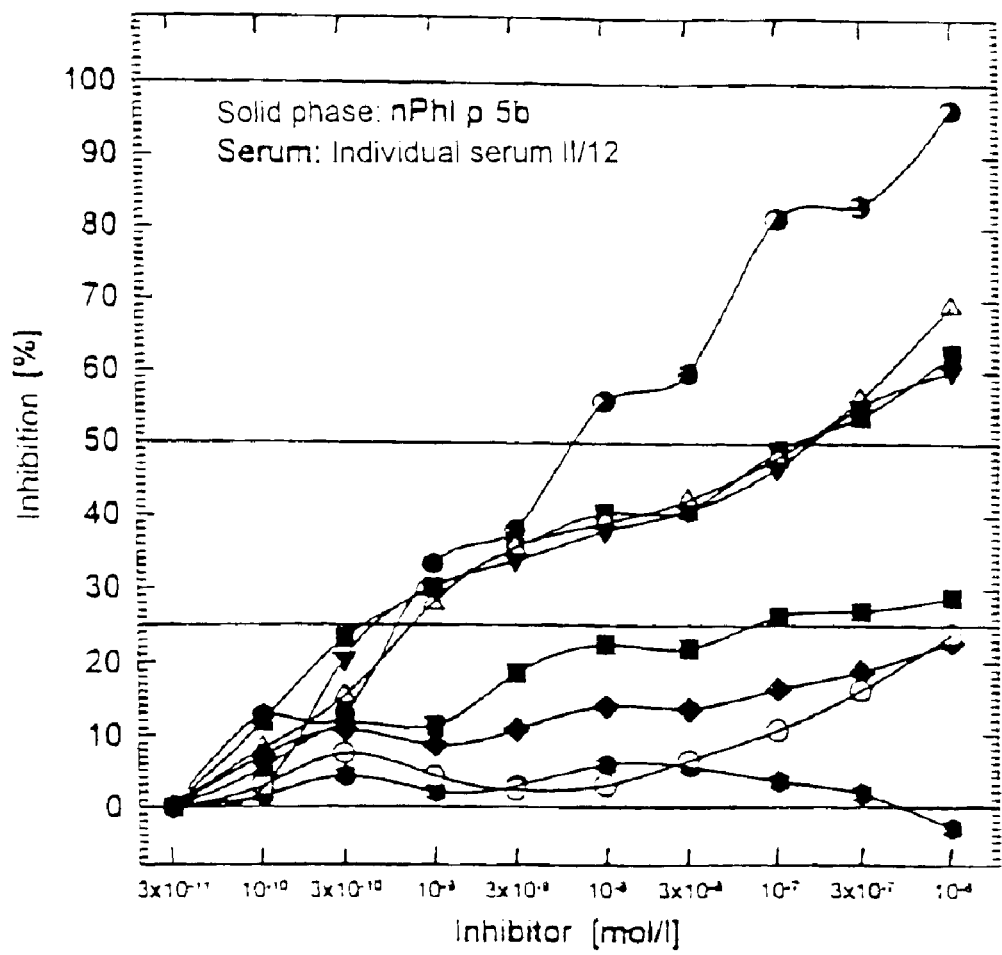

FIG. 4 shows EAST inhibition curves of the Phl p 5b mutants using the allergic patient serum pool 11/12.

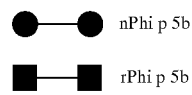

-continued

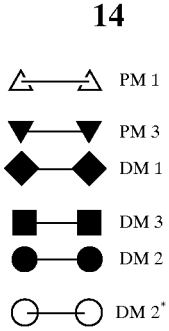

Figure 5:
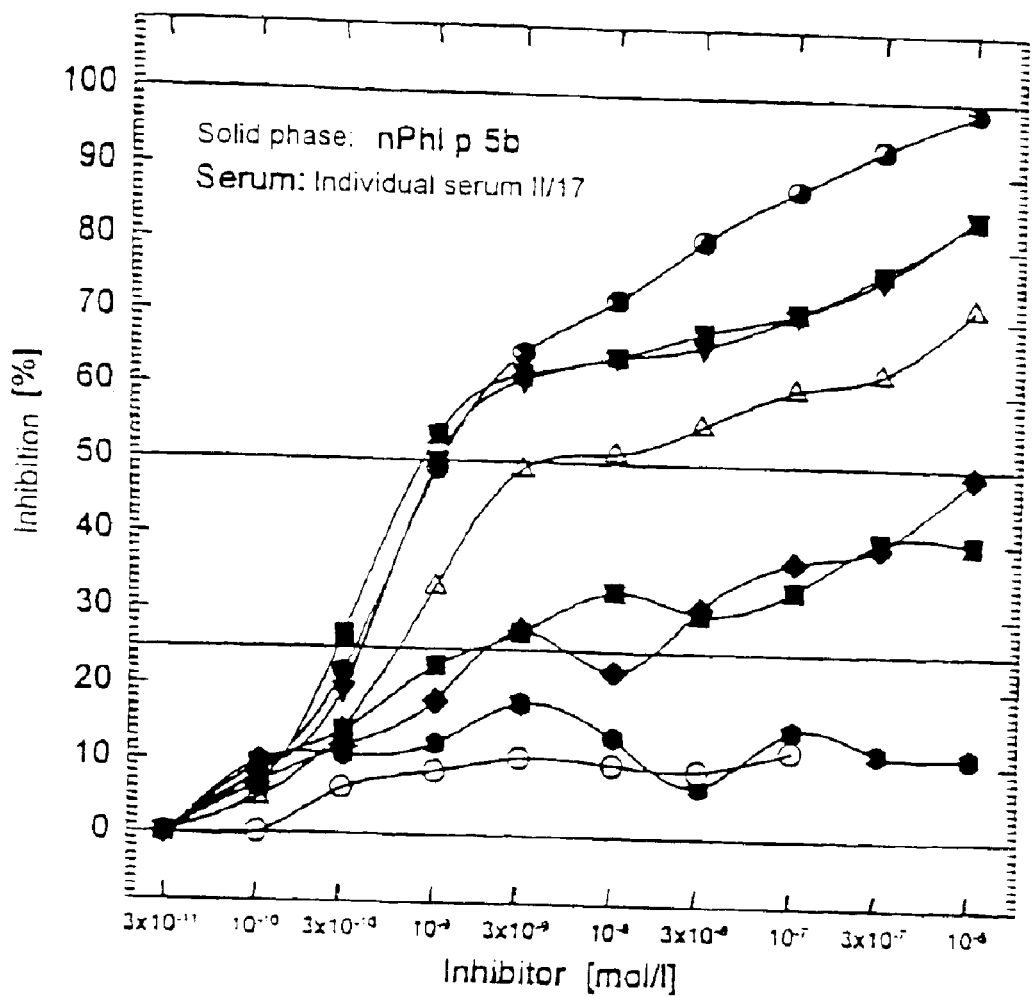

FIG. 5 shows EAST inhibition curves of the Phl p 5b mutants using the allergic patient serum pool 11/17.

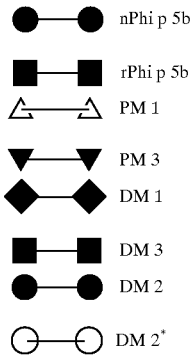

Figure 6:
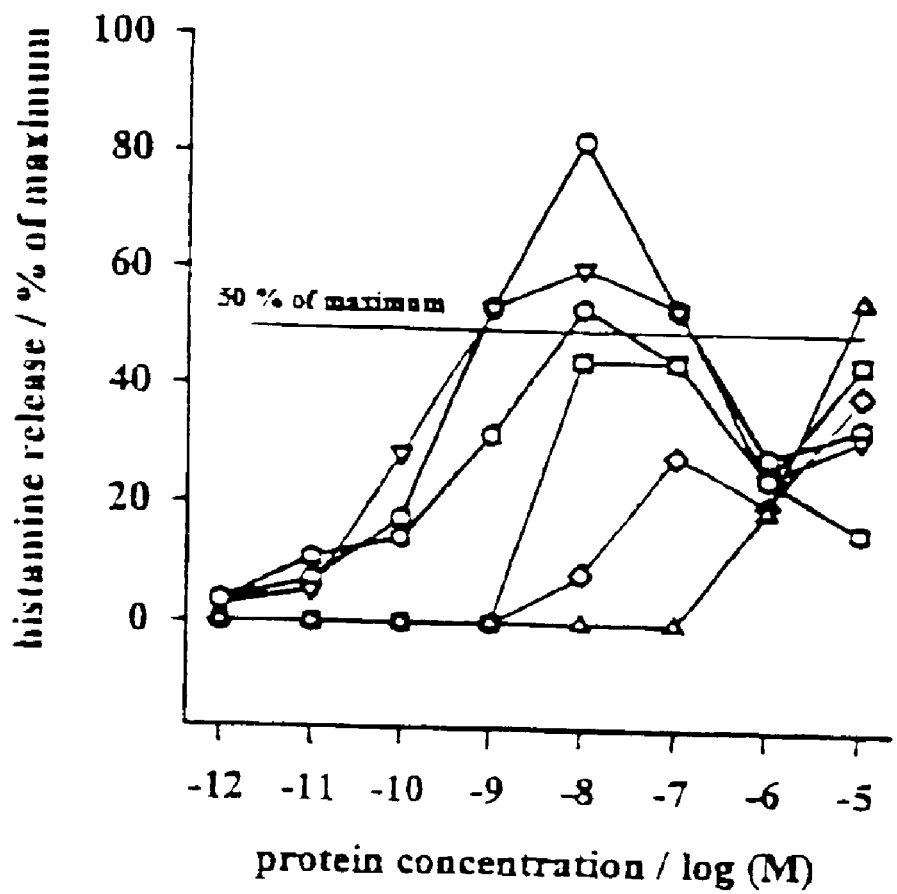

FIG. 6 shows release of histamine from human basophils after reaction with the allergens and allergen mutants.

EXAMPLE 1

Identification of the T Cell Epitopes for Determining the T Cell-reactive Regions of the Main Grass Pollen Allergen Phl ph5

Patients who had case histories of the typical symptomatology of a grass pollen allergy (rhinitis) and who gave a positive skin test (prick test) were selected for establishing T cell lines (TCL) and T cell clones (TCC) which react with the main group 5 grass pollen allergen of timothy grass (*Phleum pratense*) Phl p5. These patients had circulating specific IgE antibodies with a RAST class ≦3.

40 ml of heparinized blood were obtained from each patient. Peripheral mononuclear cells (PBMC) were then isolated from this blood sample by means of the customary method using density gradient centrifugation. Analogous cell isolations were carried out at a later stage when it was necessary to obtain irradiated autologous antigen-presenting cells (APC) for characterizing the TCL and TCC further. After the PBMC had been counted, TCL which reacted to group 5 allergens in vitro were established as follows and as has already been described in detail elsewhere (Lit. 1): in each well of 24-well microculture plates, from 1.5 to 2.0× $10^6$ PBMC in 1 ml of culture medium (UltraCulture) were stimulated for 7 days in the added presence of natural Phl p5 allergens (in each case 10 µg/well) which had been purified by immunoaffinity chromatography. A total of from 8 to 10 of these cultures were set up. The isolation of Phl p5 by means of immunoaffinity chromatography has been described in detail (Lit. 2). At the end of the 7 days of culture, IL-2 (from 10 to 20 IU/well) was added to the cell cultures for a further 5 to 7 days. All the individual cultures were then pooled and the T cell blasts were enriched by means of density gradient centrifugation; the TCL which were obtained were then tested in a specific lymphocyte proliferation test (see Lit. 1 as well). For this, 2×10⁴/ml TCL blasts were in each case cultured with 5×10⁴/ml irradiated autologous APCs in triplicate samples in 96-well microculture plates. 10–20 µg of Phl p5 allergen were added as the specific antigen stimulus. After 56 hours of incubation, ³H-labelled thymidine (1 µCi/well) was pipetted into the microcultures. After a further 16 hours, the radioactivity which had been incorporated into the proliferating T cell blasts was measured in a beta counter (Matrix 96). The results were calculated, as the arithmetic mean of the multiple samples, in counts per minute (cpm). The criterion for the quality of the TCL was the stimulation index, which was obtained by relating the cpm values with Phl p5 addition to those without Phl p5 addition.

After they had been selected, the TCLs were cloned (see Lit. 1). For this, 0.3 [lacuna] of TCL blasts/well were cultured in a final volume of 0.2 ml in 96-well microculture plates (round-bottomed) in the added presence of irradiated allogenic PBMC (5×10⁴/well), PHA (1.5 g/ml) and IL-2 (25 IU/ml). After 12 to 14 days, the cultures were fed with fresh irradiated PBMC, PHA and IL-2. In addition, a medium replacement, with addition of IL-2 (25 IU/ml), was carried out every 4 to 5 days. An approx. 10 day period without adding irradiated allogenic PBMC elapsed before the Phl p5-specific proliferation test was carried out. The selected TCC were then multiplied in 24-well microculture plates by being repeatedly stimulated with PHA, irradiated allogenic PBMC and IL-2 (50 IU/ml).

After a TCL had been cloned (see below), the specificity of the isolated TCCs were determined as has just been described. Stimulation indices of at least 5 were rated as being positive for the TCCs. The determination of T cell epitopes for defining the T cell-reactive regions on group 5 allergens was also carried out using specific proliferation tests, with 1–2 µg of synthesized dodecapeptide/ml being used for this purpose in each case (see below).

A total of 86 overlapping synthetic dodecapeptides, which were prepared on the basis of the known primary structure of the Phl p 5b allergen as determined by Bufe et al. (Lit. 3), were used for determining the T cell epitopes. These peptides were prepared using a commercial synthesis kit supplied by CHIRON Mimotopes Peptide Systems/Clayton, Australia. The amino acid sequences of these peptides had a degree of overlap of 9 amino acids (Tab. 1). The reaction of TCC to one of the peptides used in the specific proliferation test was assessed as being positive when the calculated stimulation index was at least 5.

TCCs from 18 patients who were allergic to grass pollen were included in the investigations. From these, success was achieved in isolating 54 T cell clones which reacted specifically with the dodecapeptides which were based on the Phl p 5b sequence. Analysis of these TCCs shows that reconfiguration of peptide ligands is clearly concentrated in 3 immunodominant T cell-reactive regions. Of the 54 T cell clones, 46, corresponding to 85%, react with the peptides of the 3 immunodominant T cell-reactive regions A, B and C of Phl p 5b (Tab. 1a). Only 8 T cell clones reacted with 5 different peptide ligands, with 3 peptides in each case being recognized by 2 different clones. The immuno-dominant T cell-reactive region A encompasses a peptide (27 mer) which corresponds to positions 181–207 and which has a core region consisting of amino acids 181–195. 28 of the 54 Phl p 5b-reactive TCCs, corresponding to 51%, only react with this immunodominant region A.

9 (17%) and 9 (17%) of the T cell clones react with the T cell-reactive regions C (position 16–48, 33 mer) and B (position 133–150), respectively. This concentration of the TH cells of the investigated panel of allergic patients on the recognition of 3 immunodominant T cell-reactive regions of the main allergen Phl p 5b makes it possible to construct Phl p 5b mutants in which these regions are not affected by the point mutations, deletion mutations or addition mutations. This creates the prerequisite for these allergen mutants to react specifically with the allergen-reactive TH cells which are present in allergic patients and to exert a therapeutic influence on these cells.

TABLE 1

Dodecapeptides which are based n the Phl p 5b sequence and which are used

| | | |
|---|---|---|
| 1 | ACAGYAPATPAA | (SEQ ID NO 1) |
| 2 | GYAPATPAAAGA | (SEQ ID NO 2) |
| 3 | PATPAAAGAAAG | (SEQ ID NO 3) |
| 4 | PAAAGAAAGKAT | (SEQ ID NO 4) |
| 5 | AGAAAGKATTEE | (SEQ ID NO 5) |
| 6 | AAGKATTEEQKL | (SEQ ID NO 6) |
| 7 | KATTEEQKLIED | (SEQ ID NO 7) |
| 8 | TEEQKLIEDINV | (SEQ ID NO 8) |
| 9 | QKLIEDINVGFK | (SEQ ID NO 9) |
| 10 | IEDINVGFKAAV | (SEQ ID NO 10) |
| 11 | INVGFKAAVAAA | (SEQ ID NO 11) |
| 12 | GFKAAVAAAASV | (SEQ ID NO 12) |
| 13 | AAVAAAASVPAA | (SEQ ID NO 13) |
| 14 | AAAASVPAADKF | (SEQ ID NO 14) |
| 15 | ASVPAADKFKTF | (SEQ ID NO 15) |
| 16 | PAADKFKTFEAA | (SEQ ID NO 16) |
| 17 | DKFKTFEAAFTS | (SEQ ID NO 17) |
| 18 | KTFEAAFTSSSK | (SEQ ID NO 18) |
| 19 | EAAFTSSSKAAA | (SEQ ID NO 19) |
| 20 | FTSSSKAAAAKA | (SEQ ID NO 20) |
| 21 | SSKAAAAKAPGL | (SEQ ID NO 21) |
| 22 | AAAAKAPGLVPK | (SEQ ID NO 22) |
| 23 | AKAPGLVPKLDA | (SEQ ID NO 23) |
| 24 | PGLVPKLDAAYS | (SEQ ID NO 24) |
| 25 | VPKLDAAYSVAY | (SEQ ID NO 25) |
| 26 | LDAAYSVAYKAA | (SEQ ID NO 26) |
| 27 | AYSVAYKAAVGA | (SEQ ID NO 27) |
| 28 | VAYKAAVGATPE | (SEQ ID NO 28) |
| 29 | KAAVGATPEAKF | (SEQ ID NO 29) |
| 30 | VGATPEAKFDSF | (SEQ ID NO 30) |
| 31 | TPEAKFDSFVAS | (SEQ ID NO 31) |
| 32 | AKFDSFVASLTE | (SEQ ID NO 32) |
| 33 | DSFVASLTEALR | (SEQ ID NO 33) |
| 34 | VASLTEALRVIA | (SEQ ID NO 34) |
| 35 | LTEALRVIAGAL | (SEQ ID NO 35) |
| 36 | ALRVIAGALEVH | (SEQ ID NO 36) |
| 37 | VIAGALEVHAVK | (SEQ ID NO 37) |
| 38 | GALEVHAVKPVT | (SEQ ID NO 38) |
| 39 | EVHAVKPVTEEP | (SEQ ID NO 39) |
| 40 | AVKPVTEEPGMA | (SEQ ID NO 40) |
| 41 | PVTEEPGMAKIP | (SEQ ID NO 41) |
| 42 | EEPGMAKIPAGE | (SEQ ID NO 42) |
| 43 | GMAKIPAGELQI | (SEQ ID NO 43) |
| 44 | KIPAGELQIIDK | (SEQ ID NO 44) |
| 45 | AGELQIIDKIDA | (SEQ ID NO 45) |
| 46 | LQIIDKIDAAFK | (SEQ ID NO 46) |
| 47 | IDKIDAAFKVAA | (SEQ ID NO 47) |
| 48 | IDAAFKVAATAA | (SEQ ID NO 48) |
| 49 | AFKVAATAAATA | (SEQ ID NO 49) |
| 50 | VAATAAATAPAD | (SEQ ID NO 50) |
| 51 | TAAATAPADDKF | (SEQ ID NO 51) |
| 52 | ATAPADDKFTVF | (SEQ ID NO 52) |
| 53 | PADDKFTVFEAA | (SEQ ID NO 53) |
| 54 | DKFTVFEAAFNK | (SEQ ID NO 54) |
| 55 | TVFEAAFNKAIK | (SEQ ID NO 55) |
| 56 | EAAFNKAIKEST | (SEQ ID NO 56) |
| 57 | FNKAIKESTGGA | (SEQ ID NO 57) |
| 58 | AIKESTGGAYDT | (SEQ ID NO 58) |
| 59 | ESTGGAYDTYKC | (SEQ ID NO 59) |
| 60 | GGAYDTYKCIPS | (SEQ ID NO 60) |
| 61 | YDTYKCIPSLEA | (SEQ ID NO 61) |
| 62 | YKCIPSLEAAVK | (SEQ ID NO 62) |
| 63 | IPSLEAAVKQAY | (SEQ ID NO 63) |

TABLE 1-continued

Dodecapeptides which are based n the Phl p 5b sequence and which are used

| | | |
|---|---|---|
| 64 | LEAAVKQAYAAT | (SEQ ID NO 64) |
| 65 | AVKQYAATYAA | (SEQ ID NO 65) |
| 66 | QAYAATVAAAPQ | (SEQ ID NO 66) |
| 67 | AATVAAAPCVKY | (SEQ ID NO 67) |
| 68 | VAAAPCVKYAVF | (SEQ ID NO 68) |
| 69 | APQVKYAVFEAA | (SEQ ID NO 69) |
| 70 | VKYAVFEAALTK | (SEQ ID NO 70) |
| 71 | AVFEAALTKAIT | (SEQ ID NO 71) |
| 72 | EAALTKAITAMS | (SEQ ID NO 72) |
| 73 | LTKAITAMSEVQ | (SEQ ID NO 73) |
| 74 | AITAMSEVQKVS | (SEQ ID NO 74) |
| 75 | AMSEVQKVSQPA | (SEQ ID NO 75) |
| 76 | EVQKVSOPATGA | (SEQ ID NO 76) |
| 77 | KVSQPATGAATV | (SEQ ID NO 77) |
| 78 | QPATGAATVAAG | (SEQ ID NO 78) |
| 79 | TGAATVAAGAAT | (SEQ ID NO 79) |
| 80 | ATVAAGAATTAA | (SEQ ID NO 80) |
| 81 | AAGAATTAAGAA | (SEQ ID NO 81) |
| 82 | AATTAAGAASGA | (SEQ ID NO 82) |
| 83 | TAAGAASGAATV | (SEQ ID NO 83) |
| 84 | GAASGAATVAAG | (SEQ ID NO 84) |
| 85 | SGAATVAAGGYK | (SEQ ID NO 85) |
| 86 | GAATVAAGGYKV | (SEQ ID NO 86) |

TABLE 1a

Mapping the T cell-reactive regions of the main grass pollen allergen Phl p 5

| TCC | Stimulating peptide ligands (12 mers) | Immunodominant T cell-reactive region | | | Minor epitope |
|---|---|---|---|---|---|
| | | A | B | C | |
| DW 8 | 139–150 | + | | | |
| DW 14 | 196–207 | + | | | |
| DW 16 | 181–192, 184–195 | + | | | |
| DW 23 | 181–192 | + | | | |
| DW 25 | 181–192, 184–195 | + | | | |
| DW 28 | 184–195 | + | | | |
| CBH 1 | 211–222, 214–225 | | | | + |
| CBH 10 | 211–222 | | | | + |
| JR 6a | 22–33, 25–36 | | | + | |
| JR 6b | 136–147, 139–150 | + | | | |
| JR 7a | 28–39, 31–42 | | | + | |
| JR 7b | 136–147, 139–150 | + | | | |
| JR 9 | 181–192, 184–195 | + | | | |
| JR 10 | 19–30 | | | + | |
| JR 11 | 49–60 | | | | + |
| JR 13 | 181–192, 184–195 | + | | | |
| JR 15 | 181–192, 184–195 | + | | | |
| JR 19a | 31–42 | | | + | |
| JR 19b | 136–147 | + | | | |
| JR 24 | 97–108, 100–111 | | | | + |
| JR 25 | 181–192, 184–195 | + | | | |
| JR 27 | 184–195 | + | | | |
| KS 1 | 181–192, 194–195 | + | | | |
| KS 2 | 181–192, 194–195 | + | | | |
| KS 3 | 181–192, 194, 195 | + | | | |
| KS 4 | 181–192, 194–195 | + | | | |
| KS 5 | 181–192, 194–195 | + | | | |
| KSE 18 | 43–54 | | | | + |
| UD 6 | 112–123 | | | | + |
| GE 4 | 136–147, 139–150 | + | | | |
| GE 7 | 136–147 | + | | | |
| GE 12 | 37–48 | | | + | |
| AS 4 | 181–192, 184–195 | + | | | |
| AS 5 | 181–192, 184–195 | + | | | |
| UZH 2 | 136–147, 139–15 | + | | | |
| UZ 25 | 97–108 | | | | + |
| CB 1 | 190–201, 193–204 | + | | | |
| CB 2 | 181–192, 184–195 | + | | | |
| CB 7 | 25–36 | | | + | |
| CB 10 | 181–192, 184–195 | + | | | |
| CB 14 | 181–192 | + | | | |
| MF 11 | 184–195 | + | | | |
| AH 19 | 16–27 | | | + | |
| AH 26 | 139–150 | | + | | |
| JMD 3 | 133–144 | | + | | |
| 45 | | A22 | 9B | 7c | 7 |
| II 3.2A 12 | 31–42 | | | + | |
| II 12.7F11 | 196–207 | + | | | |
| II 12.5C10 | 187–198 | + | | | |
| II 17.9E5 | 184–195 | + | | | |
| II 17.1D8 | 184–195 | + | | | |
| II 17.11C2 | 184–195 | + | | | |
| II 17.19A1 | 193–204 | + | | | |
| II 17.12F5 | 25–36 | | | + | |
| II 17.3C10 | 49–60, 52–63 | | | | + |
| 54 | | 28 | 9 | 9 | 8 |

Literature
1. Müller WD, Karamfilov T, Fahlbusch B, Vogelsang H, Jäger L: "Analysis of human T cell clones reactive with group V grass pollen allergens". Int. Arch. Allergy Immunol. 1994, 105:391–396.
2. Jung K, Fahlbusch B, Müller WD, Hermann D, Diener C, Jäger L: "Isolation of timothy (Phleum pratense) allergens using affinity chromatography with monoclonal antibodies". Allergy Immunol (Leipzig) 1989, 35:287–294.
3. Bufe A, Schramm G, Keown MB, Schlaak M, Becker WM: "Major allergen Phl p 5b in timothy grass is a novel pollen Rnase". FEBS Letters 1995, 263:6–12.

EXAMPLE 2

Preparation of Point Mutants PM1, PM2 ($D^{48} \to L$, $K^{50} \to A$) and PM3 ($A^{13} \to C$) of rPhl p 5b

PM2

Plasmid pGS13 was used as the starting vector. This is the pMalc vector (Biolabs) which contains the cDNA for the wt rPHl p 5b which is cloned between Bam EI and Hind III sites. Fragments 1 (bp: 1–153) and 2 (bp: 141–1374) of the cDNA for the rPHl p 5b were amplified in a PCR reaction. The following primers (restriction sites are underlined) were used for this reaction:

Fragment 1

PHl p 5b sense:

Phl p 5b sense 5'-ATAT<u>GGATCC</u>ATCGAGGGAAGGGCCGATGCCGGCTACGCC-3' (SEQ ID NO 94)

MP1 antisense: 5'-GAAC<u>GCTAGC</u>GCCGCAGGG ACG CTGGC-3' (SEQ ID NO 95)

Fragment 2

MP1 sense: 5'-GC<u>GCTAGC</u>GTTCAAGACCTTCGAG-3' (SEQ ID NO 96)

Phl p 5B antisense: 5'-ATAT<u>AAGCTT</u>TCCTCT GAAGGAAGGCAACCC-3' (SEQ ID NO 97)

As compared with the wt sequence, the two mutagenesis primers Mp1 sense and MP1 antisense contain 6 base replacements which additionally give rise to a new restriction cleavage site for the enzyme Nhe I.

The amplified fragment 1 was digested with Bam HI and Nhe I and cloned into vector pUH89 (Jekel et al., Gene: 154: 55–59; 1995). The resulting plasmid, pGS10, was restricted once again with Nhe I/Hind III, and fragment 2 (Nhe I/Hind III) was incorporated into these cleavage sites. This plasmid, pGS11, comprises the complete cDNA encoding rPh1 p 5b but containing the desired base replacements. In order to express the point mutant rPhl p 5b PM2, the mutated cDNA was recloned between the Bam HI and Hind III cleavage sites of the expression vector pMalc. The resulting plasmid was designated pGS21.

The point mutant rPhl p 5b PM1 was prepared in analogy with PM2. It contains, as the result of a PCR error, an additional point mutation $N^{32} \rightarrow D$.

In order to clone this point mutant, the entire cDNA for rPhl p 5b in vector pGS13 was amplified in a PCR using the following primers.

PCysM1: 5'ATAGGATCCATCGAGGGTAGGGCCGAT GCCGGCTACGCCCGGCCACCCCGGCTGCATGGGAG CG-3' (SEQ ID NO 93)

Phl p 5b antisense: see above.

As compared with the wt sequence, the mutagenesis primer PCysM1 contains 3 base substitutions which lead to an alanine residue being replaced with a cysteine residue and which at the same time give rise to a new restriction cleavage site for the enzyme Sph I. The PCR product was cloned directly into the pMalc expression vector (Bam HI/Hind III). The resulting vector was designated pCysM1. The success of the mutagenesis was checked in a restriction analysis using Sph I.

EXAMPLE 3

Preparation of the Deletion Mutants DM1 ($\Delta K^{50}$–$p^{132}$, $D^{49} \rightarrow L$), DM2 ($\Delta F^{51}$–$G^{178}$, $D^{49} \rightarrow L$, $K^{50} \rightarrow A$) and DM3 ($\Delta A^{154}$–$T^{177}$, $A^{220} \rightarrow T$)

Plasmid pGS21 (see above) was used as the starting vector for cloning the deletion mutant DM1. The bp 399–1374 fragment of the cDNA for rPhl p 5b was amplified in a PCR using the following primers:

MP2 sense: 5'-GCTAGCCGGCGAGCTGCAGAT CATCG-3' (SEQ ID NO 99)

Phl p 5b antisense: see above.

Vector pGS21 was restricted with Nhe I and BamHI and separated from the excised fragment. The PCR product, which had also been restricted with Nhe I and BAM HI, was then ligated into the residual vector. The vector which resulted from this, i.e. pDM1, contains the rPhl p 5b cDNA which has a deletion of 252 bp and which encodes the deletion mutant rPhl p 5bDMl. Deletion mutants DM2 and DM3 were prepared in an analogous manner.

EXAMPLE 4

Use of the EAST Inhibition Test to Demonstrate the Diminished Allergenicity (IgE Reactivity) of the Recombinant Ph1 p 5b mutants The binding of the allergens by the IgE antibodies is the basic prerequisite for the allergen-specific activation of the effector cells (mast cells, basophils, inter alia) in type I allergy. The allergen-specific inhibition of the enzyme/ allergen sorbent test (EAST) is the best means for qualitatively and quantitatively recording the binding of the allergens to IgE anti-bodies. The EAST inhibition test is carried out as follows. Microtitre plates are coated with allergen (natural or recombinant Phl p 5 or Phl p 5b) (1 µg/ml). After the unbound allergen molecules have been removed by washing, non-specific plastic binding sites are blocked with bovine serum albumin (0.5%). Anti-IgE from allergic patients, as a representative pool of 10–30 donors or as an individual serum, is incubated, in a suitable dilution, with the allergen-coated microtritre plates. The bound allergen-specific IgE antibodies are quantified using enzyme-coupled anti-IgE antibodies (e.g. alk. phosphatase-a-IgE antibodies). This binding is inhibited by soluble allergen or the substance to be tested (allergen mutants) in dependence on the concentration. The inhibition curve obtained with the purified natural allergen Ph1 p 5b is used as the reference.

Figure 1:
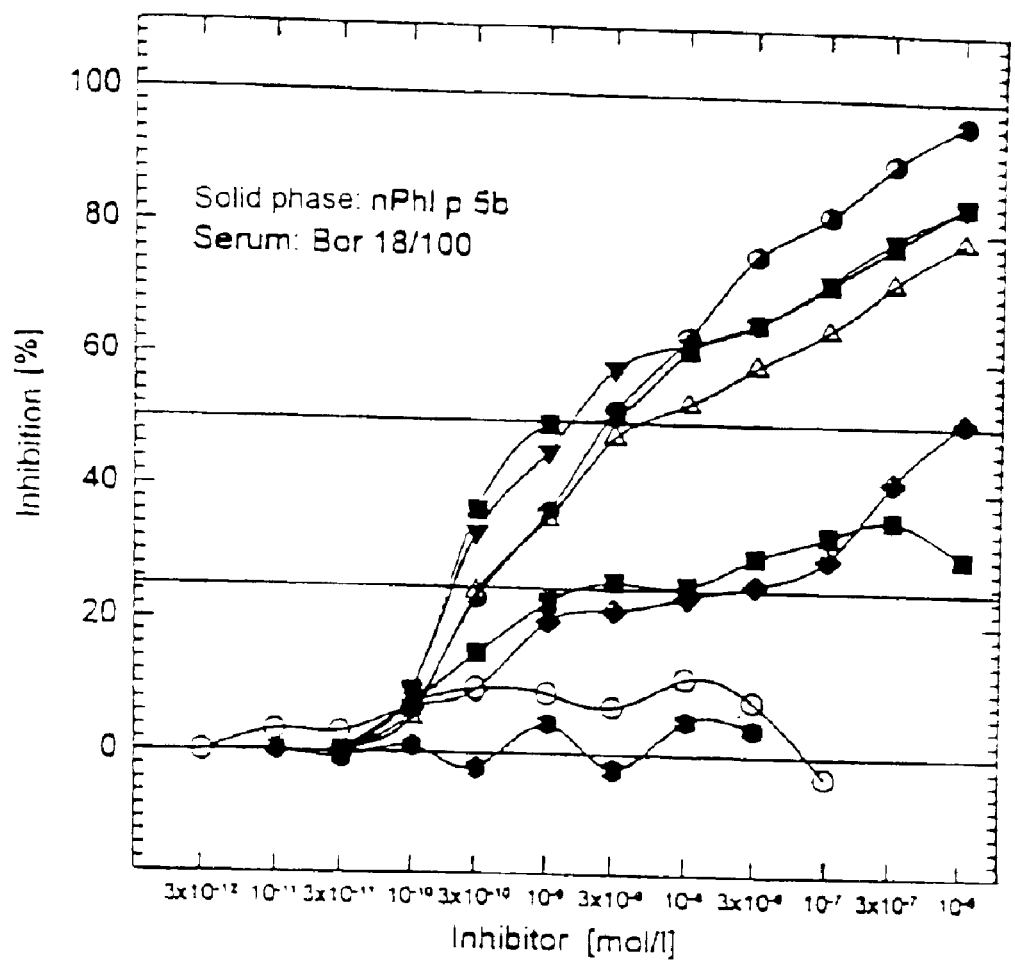
FIG. 1 shows EAST inhibition curves of the Phl p 5b mutants using the allergic patient serum pool Bor 18/100. The inhibitors are.

The inhibition curves depicted in FIG. 1 are obtained with the representative allergen patient serum pool Bor 18/100 (20 donors).

rPh1 p 5b (wild type) and PM3 exhibit binding curves which are similar to that obtained with natural Ph1 p 5b which has been purified by affinity chromatography. Minor differences are visible due to a better inhibitory effect in the lower range and to poorer inhibition at high concentrations. While the reason for this is unknown, it might be accounted for by confirmational epitopes which differ to a minor extent.

Point mutant PM1 exhibits this effect in the higher range to a somewhat greater degree. The deletion mutants DM1 and DM3 exhibit a markedly decreased inhibitory effect. This substantiates the strongly reduced allergenicity of these allergen mutants, which, as a consequence, are comparable with chemically modified allergens (allergoids).

Deletion mutants DM2 and DM2+ exhibit an extremely low inhibitory effect on the allergen-IgE reaction. This shows that the allergenicity of these mutants has to a large extent been eliminated. While a different serum pool from allergic patients (We 6/97) and also the individual sera from allergic patients II3, II12 and II17 exhibit sight variations in their inhibitory curves with the mutants, they nevertheless confirm that deletion mutants DM1 and DM3 exhibit greatly reduced allergenicity (FIGS. 2–5). Apart from a low residual activity, the inhibitory effect of deletion mutants DM2 and $DM2^+$ is eliminated. Point mutations PM1 and PM3 exhibit either no reduction, or only a reduction which is for the most part slight, in allergenicity (e.g. PM1 with pool We 6/97 and individual serum II 17). the inhibitory capacity of the modified allergens can be quantified by calculating the Prel values at 25% or 50% inhibition (1). The corresponding inhibitory values, and also the allergenic potency (Prel) measured at 25 or 50% inhibition, are shown for the serum pools and the individual sera in Tables 2–6.

Deletion Mutants DM2 and $DM2^+$ show their loss of allergenicity by their Prel values, which are extremely low or can no longer be determined in a meaningful manner. While point mutations PM1 and PM3 exhibit a partial loss of allergenicity, this loss is not adequate for practical use. Deletion mutants DM1 and DM3 exhibit a marked reduction in allergenicity. The reduction in IgE reactivity is superior to, or comparable with, that of the previously known chemically modified allergens and thereby makes these mutants particularly suitable candidates for immunotherapy.

Literature

Anderson MC and Baer H: Methodology for RAST inhibition. Food and Drug Administration, Bethesda, Md., U.S.A. (1986).

TABLE 2

Allergenic potency ($P_{rel.}$) of the recombinant Phl p 5b mutants as compared with that of recombinant and native Phl p 5b using the allergic patient serum pool Bor 18/100

| Inhibitor | Inhibition value[1] [mol/l] 25% | 50% | Allergenic potency $(P_{rel})$[2] 25% | 50% |
|---|---|---|---|---|
| n Phl p 5b | $3.3 \times 10^{-10}$ | $4.2 \times 10^{-9}$ | 1.000 | 1.000 |
| r Phl p 5b | $2.0 \times 10^{-10}$ | $5.0 \times 10^{-9}$ | 1.709 | 0.8410 |
| PM1 | $4.5 \times 10^{-10}$ | $1.2 \times 10^{-8}$ | 0.739 | 0.3490 |
| PM3 | $2.0 \times 10^{-10}$ | $4.8 \times 10^{-9}$ | 1.641 | 0.8640 |
| DM1 | $8.6 \times 10^{-9}$ | $2.8 \times 10^{-8}$ | 0.039 | 0.0015 |
| DM2 | $8.3 \times 10^{13}$ | $2.3 \times 10^{38}$ | $4.0 \times 10^{-23}$ | $1.8 \times 10^{-45}$ |
| DM3 | $1.2 \times 10^{-9}$ | $4.1 \times 10^{-6}$ | 0.028 | 0.0001 |
| DM2+ | $5.0 \times 10^{23}$ | $2.3 \times 10^{66}$ | $6.7 \times 10^{-34}$ | $2.0 \times 10^{-75}$ |

[1]Inhibition values: Concentrations of the inhibitors at 25% and 50% inhibition, respectively
[2]Allergenic potency: Relative to native Phlp5b at 25% and 50% inhibition, respectively

TABLE 3

Allergenic potency ($P_{rel.}$) of the recombinant Phl p 5b mutants as compared with that of recombinant and native Phl p 5b using the allergic patient serum pool We 6/97

| Inhibitor | Inhibition value[1] [mol/l] 25% | 50% | Allergenic potency $(P_{rel})$[2] 25% | 50% |
|---|---|---|---|---|
| n Phl p 5b | $5.1 \times 10^{-10}$ | $6.1 \times 10^{-9}$ | 1.000 | 1.000 |
| r Phl p 5b | $3.0 \times 10^{-10}$ | $1.4 \times 10^{-6}$ | 1.697 | 0.4400 |
| PM1 | $1.2 \times 10^{-9}$ | $1.2 \times 10^{-7}$ | 0.415 | 0.0510 |
| PM3 | $8.3 \times 10^{-10}$ | $3.0 \times 10^{-8}$ | 0.611 | 0.2030 |
| DM1 | $2.3 \times 10^{-8}$ | $1.7 \times 10^{-5}$ | 0.022 | 0.0004 |
| DM2 | $1.9 \times 10^{8}$ | $2.7 \times 10^{21}$ | $2.6 \times 10^{-25}$ | $2.3 \times 10^{-30}$ |
| DM3 | $5.1 \times 10^{-9}$ | $2.9 \times 10^{-8}$ | 0.099 | 0.0020 |
| DM2+ | $4.6 \times 10^{-7}$ | $1.5 \times 10^{-3}$ | 0.001 | $4.0 \times 10^{-8}$ |

[1]Inhibition values: Concentrations of the inhibitors at 25% and 50% inhibition, respectively
[2]Allergenic potency: Relative to native Phlp5b at 25% and 50 inhibition, respectively

TABLE 4

Allergenic potency ($P_{rel.}$) of the recombinant Phl p 5b mutants as compared with that of recombinant and native Phl p 5b using the individual allergic patient serum II/3

| Inhibitor | Inhibition value[1] [mol/l] 25% | 50% | Allergenic potency $(P_{rel})$[2] 25% | 50% |
|---|---|---|---|---|
| n Phl p 5b | $5.1 \times 10^{-10}$ | $5.9 \times 10^{-9}$ | 1.000 | 1.000 |
| r Phl p 5b | $5.6 \times 10^{-10}$ | $1.4 \times 10^{-8}$ | 0.9030 | 0.4190 |
| PM1 | $8.6 \times 10^{-10}$ | $1.9 \times 10^{-8}$ | 0.5950 | 0.3140 |
| PM3 | $5.5 \times 10^{-10}$ | $1.5 \times 10^{-8}$ | 0.9220 | 0.3990 |
| DM1 | $1.2 \times 10^{-8}$ | $1.7 \times 10^{-8}$ | 0.0420 | 0.0035 |
| DM2 | $6.6 \times 10^{10}$ | $5.2 \times 10^{27}$ | $7.7 \times 10^{-20}$ | $1.1 \times 10^{-38}$ |
| DM3 | $1.1 \times 10^{-6}$ | 0.032 | 0.0004 | $1.8 \times 10^{-7}$ |
| DM2+ | $2.1 \times 10^{-6}$ | 0.010 | 0.0002 | $5.9 \times 10^{-7}$ |

[1]Inhibition values: Concentrations of the inhibitors at 25% and 50% inhibition, respectively
[2]Allergenic potency: Relative to native Phlp5b at 25% and 50% inhibition, respectively

TABLE 5

Allergenic potency ($P_{rel.}$) of the recombinant Phl p 5b mutants as compared with that of recombinant and native Phl p 5b using the individual allergic patient serum II/12

| Inhibitor | Inhibition value[1] [mol/l] 25% | 50% | Allergenic potency $(P_{rel})$[2] 25% | 50% |
|---|---|---|---|---|
| n Phl p 5b | $5.2 \times 10^{-10}$ | $6.8 \times 10^{-9}$ | 1.000 | 1.000 |
| r Phl p 5b | $8.7 \times 10^{-10}$ | $7.3 \times 10^{-8}$ | 0.597 | 0.093 |
| PM1 | $1.3 \times 10^{-9}$ | $8.3 \times 10^{-8}$ | 0.391 | 0.082 |
| PM3 | $1.3 \times 10^{-9}$ | $9.1 \times 10^{-8}$ | 0.389 | 0.075 |
| DM1 | $1.5 \times 10^{-5}$ | 68.0 | $3.4 \times 10^{-5}$ | $1.0 \times 10^{-10}$ |
| DM2 | $3.8 \times 10^{10}$ | $4.4 \times 10^{10}$ | $1.4 \times 10^{-19}$ | $1.6 \times 10^{-39}$ |
| DM3 | $4.5 \times 10^{-9}$ | 0.0001 | 0.012 | $5.7 \times 10^{-5}$ |
| DM2+ | 196.0 | $7.4 \times 10^{14}$ | $2.6 \times 10^{-12}$ | $9.2 \times 10^{-25}$ |

[1]Inhibition values: Concentrations of the inhibitors at 25% and 50% inhibition, respectively
[2]Allergenic potency: Relative to native Phlp5b at 25% and 50% inhibition, respectively

TABLE 6

Allergenic potency ($P_{rel.}$) of the recombinant Phl p 5b mutants as compared with that of recombinant and native Phl p 5b using the individual allergic patient serum II/17

| Inhibitor | Inhibition value[1] [mol/l] 25% | 50% | Allergenic potency $(P_{rel})$[2] 25% | 50% |
|---|---|---|---|---|
| n Phl p 5b | $2.2 \times 10^{-10}$ | $2.6 \times 10^{-9}$ | 1.000 | 1.000 |
| r Phl p 5b | $2.1 \times 10^{-10}$ | $4.7 \times 10^{-9}$ | 1.045 | 0.5450 |
| PM1 | $6.4 \times 10^{-10}$ | $2.2 \times 10^{-9}$ | 0.336 | 0.1190 |
| PM3 | $2.5 \times 10^{-10}$ | $5.5 \times 10^{-9}$ | 0.855 | 0.4680 |
| DM1 | $6.5 \times 10^{-9}$ | $2.0 \times 10^{-9}$ | 0.033 | 0.0010 |
| DM2 | 73.9 | $6.4 \times 10^{19}$ | $2.9 \times 10^{-12}$ | $4.1 \times 10^{-29}$ |
| DM3 | $5.6 \times 10^{-9}$ | $5.0 \times 10^{-8}$ | 0.038 | 0.0005 |
| DM2+ | 0.0004 | 11675.0 | $5.3 \times 10^{-7}$ | $2.2 \times 10^{-10}$ |

[1]Inhibition values: Concentrations of the inhibitors at 25% and 50% inhibition, respectively
[2]Allergenic potency: Relative to native Phlp5b at 25% and 50% inhibition, respectively

EXAMPLE 5

Reduced Histamine Release from Basophils Due to the rPhl p 5b Mutants

The ability of the point mutant PM3 which was prepared, and of deletion mutant DM1, DM2, MD2+ and DM3, to release histamine from basophils was tested and compared with that of the wild type rPhl p 5b.

Before the histamine release test was carried out, the basophilic leucocytes from the EDTA blood of an allergic patient (PS-W) were first of all enriched by means of dextran sedimentation and then adjusted to a final concentration of 100,000 basophils/ml. In order to release histamine from the basophils, 200 µl of the cell suspension were in each case incubated, at 37° C. for 40 min, with 50 µl of antigen solution. For this, the rPhl and p 5b and the mutants were employed in varying concentrations (of $10^{-5}$–$10^{-12}$ M). The histamine which was released was determined in the respective supernatants using the Pharmacia methylhistamine RIA in accordance with the manufacturer's instructions.

In the histamine release test, all the recombinant proteins investigated described the typical bell-shaped curve as their concentrations increased (FIG. 6). The point mutant did not shown any significant differences as compare with the wild type rPh1 p 5b in its ability to release histamine. The concentrations of the deletion mutants DM3, DM1 and DM2 which were required to bring about a 30% histamine release were 3-fold, 20-fold and 500-fold higher, respectively. The deletion mutants therefore unambigously exhibit a decreased ability to release histamine from basophils.

EXAMPLE 6

Demonstration of the Relativity of Recombinant pH1 p *5b* Mutants and T Cell Clones from Patients who are Allergic to Grass Pollen The reactivity of the recombinant Ph1 p *5b* mutants was tested on established T cell clones (TCCs) of known specificity. The TCCs derive from patients who are allergic to grass pollen (see Ex. 1) and are directed against the T cell-reactive regions A (FIG. 7), B (FIG. 8) and C (FIG. 9). The T cell reactivity was measured by stimulating the clones to proliferate. The results clearly show that the TCCs react specifically with the Ph1 p *5b* mutants when the relevant epitope is unaltered and, as expected, do not exhibit any reaction when the epitope is messing or is altered by a point mutation.

Table 7

Proliferative reaction of Ph1 p *5b*-reactive T cell clones (TCCs) from allergic patients with rPh1 p *5b* mutants.

Specificity: Immunodominant T cell-reactive region A

| | Epitope | Incorporation of $[^3H]$-thymidine into TCC[2)] | | | |
|---|---|---|---|---|---|
| Stimulator[1)] | present | JR 15 | JR 13 | CB 14 | CB 2 |
| Medium | – | – | – | – | – |
| n Phl p5 | + | +++ | +++ | +++ | +++ |
| r Phl p5a | (±) | – | – | + | + |
| r Phl p5b | + | +++ | +++ | +++ | +++ |
| PM1 | + | ++ | +++ | +++ | +++ |
| PM3 | + | +–+ | +++ | –++ | +++ |
| DM1 | + | +++ | +++ | +++ | +++ |
| DM2 | + | +++ | +++ | nt[3)] | nt |
| DM2⁺ | + | – | – | – | – |
| DM3 | + | +++ | +++ | nt | nt |
| PL (12 mer) | + | +++ | +++ | +++ | +++ |

[1)]Final concentration 0.3 $\mu$M
[2)]Stimulation index SI: <1 (–), 1–2 (+), 2–5 (+), 5–10 (++), >10 (+++)
[3)]n.t.: not tested

TABLE 8

Proliferative reaction of Ph1 p *5b*-reactive T cell cones (TCCs) from allergic patients with rPh1 p *5b* mutants Specificity: Immunodominant T cell-reactive region B

| | Epitope | Incorporation of $[^3H]$-thymidine into TCC[2)] | |
|---|---|---|---|
| Stimulator[1)] | present | UZH2 | DW8 |
| Medium | – | – | – |
| n Phl p5 | + | +++ | +++ |
| r Phl p5a | (±) | ± | +++ |
| r Phl p5b | + | +++ | + |
| PM1 | + | +++ | + |
| PM3 | + | +++ | ± |
| DM1 | + | +++ | + |
| DM2 | – | – | – |
| DM2⁺ | – | – | – |
| DM3 | + | +++ | + |
| PL (12 mer) | + | +++ | +++ |

-continued

[1)]Final concentration 0.3 $\mu$M
[2)]Stimulation index SI: <1 (–), 1–2 (+), 2–5 (+), 5–10 (++), >10 (+++)
[3)]n.t.: not tested

TABLE 9

Proliferative reaction of Ph1 g *5b*-reactive T cell clones (TCCs) from allergic patients with rPh1 p *5b* mutants.

Specificity: Immunodominant T cell-reactive region C

| | Epitope | Incorporation of $[^3H]$-thymidine[2)] | | | |
|---|---|---|---|---|---|
| Stimulator[1)] | present unchanged | 1st exp. | 2nd exp. | 3rd exp. | |
| Medium | – | 1 | 1 | 1 | – |
| n Phl p5 | + | 11.2 | 8.2 | 4.5 | ++ |
| r Phl p5a | – | nt | ×1 | ×1 | – |
| r Phl p5b | + | 11.0 | 7.0 | 5.5 | ++ |
| PM1 | – | ×1 | ×1 | 1.1 | – |
| PM3 | + | 7.4 | 5.9 | 4.5 | ++ |
| DM1 | + | 8.6 | 6.2 | 4.4 | ++ |
| DM2 | + | 14.4 | 9.1 | 7.1 | +++ |
| DM2⁺ | + | 12.8 | 12.1 | 11.7 | +++ |
| DM3 | + | 9.8 | 6.9 | 4.4 | ++ |
| PL (12 mer) | + | 20.9 | 16.7 | nt[3)] | +++ |

[1)]Final concentration 0.3 $\mu$M
[2)]Stimulation index SI: <1 (–), 1–2 (+), 2–5 (+), 5–10 (++), >10 (+++)
[3)]n.t.: not tested

EXAMPLE 7

Texting the Reactivity of Recombinant Ph1 p *5b* Mutants with T Cell Lines from Patients who are Allergic to Grass Pollen The oligoclonal T cell lines (TCLs) from 8 patients who were allergic to grass pollen (see Ex. 1) were established by repeated activation with natural Ph1 p *5b* (a+b) or recombinant rPh1 p *5b* or *5a+5b*.

The proliferative reaction of these TCLs was tested using the rPh1 p *5b* mutants (FIG. 10). This shows that while all the mutants activate the TCLs, there are quantitative differences. The deletion mutant DM3 exhibits a strong specific stimulation with most of the TCLs.

TABLE 10

Proliferative reaction of Ph1 p *5b*-reactive T cell lines (TCLs) from allergic patients with rPh1 p *5b* mutants.

| | Incorporation of [$^3$H]-thymidine into TCL$_s$[2] | | | | | | | |
|---|---|---|---|---|---|---|---|---|
| TCL | 1 Wöl | 2 Eic | 3 Fre | 4 Mer | 6 Mah | 5 17.4 | 7 19.2 | 8 20.1 |
| Primary stimulator Secondary activator[1] | n Phl p 5 | n Phl p 5 | n Phl p 5 | n Phl p 5 | r Phl p 5a r Phl p 5b | r Phl p 5 | r Phl p 5b | r Phl p 5b |
| n Phl p 5 | +++ | +++ | ++ | +++ | +++ | + | +++ | + |
| r Phl p 5a | − | + | + | + | ++ | nt[3] | nt | nt |
| r Phl 5b | + | + | + | + | +++ | + | +++ | +++ |
| PM1 | + | ± | + | ± | ++ | + | +++ | +++ |
| PM3 | ± | ± | + | + | ± | + | +++ | + |
| DM1 | ± | + | + | + | ++ | + | +++ | +++ |
| DM2 | ± | + | +++ | +++ | ++ | + | ++ | +++ |
| DM2+ | ± | + | + | ++ | ++ | + | + | ± |
| DM3 | ± | + | ++++ | ++ | +++ | ++ | +++ | +++ |

[1] Final concentration 0.3 µM
[2] Stimulation index SI: <1 (−), 1–2 (+), 2–5 (+), 5–10 (++), >10 (+++)
[3] n.t.: not tested Recapitulative assessment of the results described in Examples 1–7

The mapping of the epitopes of the main allergen Ph1 p 5b which are recognized by T helper cells from patients who are allergic to grass pollen has demonstrated that the T cell epitopes of the individual T cell clones (TCLs) are distributed over the entire sequence of the Ph1 p 5b. However, 3 immunodominant T cell-reactive regions which are recognized by 85% of the TCCs can be defined without difficulty (Example 1). It was possible to produce recombinant Ph1 p 5b mutants by means of point mutations (Example 2) and by means of deletion mutations (Example 3). The IgE reactivity of the point mutants (PM1 and PM3), as measured in the EAST inhibition test (Example 4), does not differ significantly from that of the wild-type Ph1 p 5b. While the IgE reactivity of the deletion mutants DM1 and DM3 is greatly reduced, it is still detectable. By contrast, the IgE binding of mutants DM2 and DM2+ is very greatly reduced. This gradual decrease in the allergenicity of the rPh1 p 5b mutants is also confirmed by the histamine release test using spec. IgE-loaded basophils from the blood of allergic patients (Example 5). The testing of the rRh1 p 5b mutants with epitope-mapped T cell clones confirms that the point mutations and deleting mutations react with, or fail to stimulate the TCLs in the expected manner (Example 6). Using oligoclonal T cell lines which were established from the blood of patients who are allergic to grass pollen by means of stimulation with Ph1 p 5, it was possible to demonstrate that mutants are able to stimulate oligoclonal TCLs of this nature (Example 7). Taking the results of the reduction in allergenicity and the retention of the T cell stimulation together, the mutants, particularly the deletion mutants, constitute recombinant allergen variants which are potentially suitable for specific immunotherapy.

The following examples relate to pharmaceutical preparations:

EXAMPLE A

Injection Vials

A solution of 100 g of an active compound or of an active compound mixture based on the modified recombinant allergens and 5 g of disodium hydrogen phosphate in 3 l of doubly distilled water is adjusted to pH 6.5 with 2N hydrochloric acid, sterilized by filtration, aliquoted into injection vials and lyophilized under sterile conditions: the vials are then sealed in a sterile manner. Each injection vial comprises 5 mg of active compound.

EXAMPLE B

Suppositories

A mixture of 20 g of an active compound in the form of the modified recombinant allergens together with 100 g of soya bean lecithin and 1400 g of cocoa butter is melted, poured into moulds and allowed to cool. Each suppository comprises 20 mg of active compound.

EXAMPLE C

Solution

A solution of 1 g of an active compound in the form of the modified recombinant allergens, 9.38 g of NaH$_2$PO$_4$ 2 H$_2$O, 28.48 g of Na$_2$HPO$_4$. 12 H$_2$O and 0.1 g of benz-alkonium chloride is prepared, in 940 ml of doubly distilled water. The solution is adjusted to pH 6.8, made up to 1.1 and sterilized by irradiation. This solution can be used in the form of eye drops.

EXAMPLE D

Ointment 500 mg of an active compound in the form of the modified recombinant allergens are mixed with 99.5 g of yellow soft paraffin under aseptic conditions.

EXAMPLE E

Tablets

A mixture of 1 kg of active compound in the form of the modified recombinant allergens, 4 kg of lactose, 1.2 kg of potato starch, 0.2 kg of talc and 0.1 kg of magnesium stearate is compressed into tablets in the customary manner such that each tablet comprises 10 mg of active compound.

EXAMPLE F

Coated tablets

Tablets are compressed in analogy with Example E and are then coated, in a customary manner, with the coating consisting of sucrose, potato starch, talc, gum tragacanth and dye.

EXAMPLE G

Capsules 2 kg of active compound in the form of the modified recombinant allergens are aliquoted, in a customary manner, into hard gelatin capsules such that each capsule comprises 20 mg of the active compound.

EXAMPLE H

Ampoules

A solution of 1 kg of active compound in the form of the modified recombinant allergens in 60 l of doubly distilled water is sterilized by filtration aliquoted into ampoules and lyophilized under sterile conditions; the ampoules are then sealed in a sterile manner. Each ampoule comprises 10 mg of active compound.

EXAMPLE I

Inhalation Spray 14 g of active compound in the form of the modified recombinant allergens are dissolved in 10 l of an isotonic solution of NaCl and the solution is aliquoted into commercially available spraying vessels which are fitted with a pump mechanism. The solution can be sprayed into the mouth or the nose. One spraying stroke (approximately 0.1 ml) corresponds to a dose of approximately 0.14 mg.

What is claimed is:

1. A modified recombinant *gramineae pollen* allergen wherein at least one of the T-cell reactive regions 16–42, 135–149 and 180–206 of the Ph1 p 5b polypeptide of SEQ ID NO: 87, is not altered.

2. A modified recombinant *gramineae pollen* allergen according to claim 1, selected from the group consisting of:

| | |
|---|---|
| PM1 ($N^{32}$ D, $D^{49}$ L, L, $K^{50}$ A) | (SEQ ID NO. 88) |
| PM2 ($D^{59}$ L, $K^{50}$ A) | (SEQ ID NO. 89) |
| PM3 ($A^{13}$ C) | (SEQ ID NO. 90) |
| DM1 ($\Delta K^{50}$ $P^{\Delta 132}$, $D^{49}$ L) | (SEQ ID NO. 91) |
| DM2 ($\Delta F^{51}$–$G^{178}$, $D^{49}$–L, $K^{50}$–A) | (SEQ ID NO. 92) and |
| DM3 ($\Delta A^{154}$–$T^{177}$, $A^{220}$ T) | (SEQ ID NO. 93). |

3. A pharmaceutical preparation for treating an IgE-mediated grass pollen allergy comprising at least one modified recombinant allergen according to claim 1 and a pharmaceutically acceptable carrier.

4. A method of immunospecific therapy for grass pollen allergies, comprising administering to a patient in need thereof a pharmaceutical composition comprising a modified recombinant *gramineae pollen* allergen according to claim 1 and a pharmaceutically acceptable carrier.

5. A method of immunospecific therapy for grass pollen allergies, comprising administering to a patient in need thereof a modified recombinant *gramineae pollen* allergen according to claim 1.

6. The pharmaceutical preparation according to claim 3 comprising a physiologically compatible salt or solvate of said recombinant modified *gramineae pollen* allergen.

7. A modified recombinant *gramineae pollen* allergen having a region which corresponds to at least one of the T-cell reactive regions 16–42, 135–149, and 180–206 of the Ph1 p 5b polypeptide of SEQ ID NO: 87. wherein at least one of said regions is not altered.

8. A modified recombinant *gramineae pollen* allergen of claim 7, wherein a combination of said regions is present and is not altered.

9. A modified recombinant *gramineae pollen* allergen according to claim 7, selected from the group consisting of:

| | |
|---|---|
| PM1 ($N^{32}$ D, $D^{49}$ L, $K^{50}$ A) | (SEQ ID NO.88) |
| PM2 ($D^{49}$ L, $K^{50}$ A) | (SEQ ID NO.89) |
| DM1 ($\Delta K^{50}$ $P^{\Delta 132}$, $D^{49}$ L) | (SEQ ID NO.91) and |
| DM3 ($\Delta A^{154}$–$T^{177}$, $A^{220}$ T) | (SEQ ID NO.93). |

10. The modified recombinant *gramineae pollen* allergen according to claim 1, wherein said modification refers to a wild type polypeptide that is altered by a substitution.

11. The modified recombinant *gramineae pollen* allergen according to claim 7, wherein said modification refers to a wild type polypeptide that is altered by a deletion.

12. The *gramineae pollen* allergen of claim 1, wherein a combination of said regions is present and is not altered.

13. A method of immunospecific therapy for grass pollen allergies, comprising administering to a patient in need thereof a modified recombinant allergen according to claim 2, wherein is DM1 or DM3.

14. A method of immunospecific therapy for grass pollen allergies, comprising administering to a patient in need thereof a modified recombinant *gramineae pollen* allergen according to claim 7.

15. A method of immunospecific therapy for grass pollen allergies, comprising administering to a patient in need thereof a modified recombinant *gramineae pollen* allergen according to claim 9 which is PM1 or PM2.

16. A method of immunospecific therapy for grass pollen allergies, comprising administering to a patient in need thereof a modified recombinant *gramineae pollen* allergen according to claim 10.

17. A method of immunospecific therapy for grass pollen allergies, comprising administering to a patient in need thereof a modified recombinant *gramineae pollen* allergen according to claim 11.

18. A method of immunospecific therapy for grass pollen allergies, comprising administering to a patient in need thereof a modified recombinant *gramineae pollen* allergen according to claim 12.

19. A *gramineae pollen* allergen of claim 1, which is a group 5 *gramineae pollen* allergen.

20. A *gramineae pollen* allergen of claim 7, which is a group 5 *gramineae pollen* allergen.

* * * * *

UNITED STATES PATENT AND TRADEMARK OFFICE
CERTIFICATE OF CORRECTION

PATENT NO.   : 6,919,086 B1
DATED        : July 19, 2005
INVENTOR(S)  : Kahlert et al.

It is certified that error appears in the above-identified patent and that said Letters Patent is hereby corrected as shown below:

Column 69,
Line 41, reads "PM2($D^{59}$L, $K^{50}$A)" should read -- PM2($^{D49}$L, $K^{50}$A) --.

Signed and Sealed this

First Day of November, 2005

JON W. DUDAS
*Director of the United States Patent and Trademark Office*

```
                          SEQUENCE LISTING

<160> NUMBER OF SEQ ID NOS: 99

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Asp Ala Gly Tyr Ala Pro Ala Thr Pro Ala Ala
  1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ala Pro Ala Thr Pro Ala Ala Ala Gly Ala
  1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ala Thr Pro Ala Ala Ala Gly Ala Ala Ala Gly
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ala Ala Ala Gly Ala Ala Ala Gly Lys Ala Thr
  1               5                  10
```

-continued

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Gly Ala Ala Ala Gly Lys Ala Thr Thr Glu Glu
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Gly Lys Ala Thr Thr Glu Glu Gln Lys Leu
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Thr Thr Glu Glu Gln Lys Leu Ile Glu Asp
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Glu Glu Gln Lys Leu Ile Glu Asp Ile Asn Val
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Lys Leu Ile Glu Asp Ile Asn Val Gly Phe Lys
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 10

Ile Glu Asp Ile Asn Val Gly Phe Lys Ala Ala Val
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Asn Val Gly Phe Lys Ala Ala Val Ala Ala Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Lys Ala Ala Val Ala Ala Ala Ala Ser Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Val Ala Ala Ala Ala Ser Val Pro Ala Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Ala Ser Val Pro Ala Ala Asp Lys Phe
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ser Val Pro Ala Ala Asp Lys Phe Lys Thr Phe
1               5                   10

<210> SEQ ID NO 16
<211> LENGTH: 12
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ala Ala Asp Lys Phe Lys Thr Phe Glu Ala Ala
 1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Lys Phe Lys Thr Phe Glu Ala Ala Phe Thr Ser
 1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Thr Phe Glu Ala Ala Phe Thr Ser Ser Ser Lys
 1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Ala Ala Phe Thr Ser Ser Ser Lys Ala Ala Ala
 1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Thr Ser Ser Ser Lys Ala Ala Ala Ala Lys Ala
 1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ser Lys Ala Ala Ala Ala Lys Ala Pro Gly Leu
```

-continued

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ala Ala Lys Ala Pro Gly Leu Val Pro Lys
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Lys Ala Pro Gly Leu Val Pro Lys Leu Asp Ala
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Gly Leu Val Pro Lys Leu Asp Ala Ala Tyr Ser
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Pro Lys Leu Asp Ala Ala Tyr Ser Val Ala Tyr
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Asp Ala Ala Tyr Ser Val Ala Tyr Lys Ala Ala
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic -continued

```
       peptide

<400> SEQUENCE: 27

Ala Tyr Ser Val Ala Tyr Lys Ala Ala Val Gly Ala
  1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Ala Tyr Lys Ala Ala Val Gly Ala Thr Pro Glu
  1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ala Ala Val Gly Ala Thr Pro Glu Ala Lys Phe
  1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Gly Ala Thr Pro Glu Ala Lys Phe Asp Ser Phe
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Pro Glu Ala Lys Phe Asp Ser Phe Val Ala Ser
  1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Lys Phe Asp Ser Phe Val Ala Ser Leu Thr Glu
  1               5                  10

<210> SEQ ID NO 33
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ser Phe Val Ala Ser Leu Thr Glu Ala Leu Arg
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Ala Ser Leu Thr Glu Ala Leu Arg Val Ile Ala
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Thr Glu Ala Leu Arg Val Ile Ala Gly Ala Leu
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Leu Arg Val Ile Ala Gly Ala Leu Glu Val His
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ile Ala Gly Ala Leu Glu Val His Ala Val Lys
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

-continued

Gly Ala Leu Glu Val His Ala Val Lys Pro Val Thr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Val His Ala Val Lys Pro Val Thr Glu Glu Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Val Lys Pro Val Thr Glu Glu Pro Gly Met Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Val Thr Glu Glu Pro Gly Met Ala Lys Ile Pro
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Glu Pro Gly Met Ala Lys Ile Pro Ala Gly Glu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Met Ala Lys Ile Pro Ala Gly Glu Leu Gln Ile
1               5                   10

<210> SEQ ID NO 44
<211> LENGTH: 12
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 44

Lys Ile Pro Ala Gly Glu Leu Gln Ile Ile Asp Lys
 1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Gly Glu Leu Gln Ile Ile Asp Lys Ile Asp Ala
 1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Ile Ile Asp Lys Ile Asp Ala Ala Phe Lys
 1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Asp Lys Ile Asp Ala Ala Phe Lys Val Ala Ala
 1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Asp Ala Ala Phe Lys Val Ala Ala Thr Ala Ala
 1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Phe Lys Val Ala Ala Thr Ala Ala Ala Thr Ala
 1               5                   10
```

```
<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Ala Ala Thr Ala Ala Ala Thr Ala Pro Ala Asp
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Ala Ala Thr Ala Pro Ala Asp Asp Lys Phe
 1               5                  10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Thr Ala Pro Ala Asp Asp Lys Phe Thr Val Phe
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Ala Asp Asp Lys Phe Thr Val Phe Glu Ala Ala
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Lys Phe Thr Val Phe Glu Ala Ala Phe Asn Lys
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

-continued

```
Thr Val Phe Glu Ala Ala Phe Asn Lys Ala Ile Lys
  1               5                  10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Ala Ala Phe Asn Lys Ala Ile Lys Glu Ser Thr
  1               5                  10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Asn Lys Ala Ile Lys Glu Ser Thr Gly Gly Ala
  1               5                  10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Lys Glu Ser Thr Gly Gly Ala Tyr Asp Thr
  1               5                  10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Ser Thr Gly Gly Ala Tyr Asp Thr Tyr Lys Cys
  1               5                  10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Ala Tyr Asp Thr Tyr Lys Cys Ile Pro Ser
  1               5                  10

<210> SEQ ID NO 61
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 61

Tyr Asp Thr Tyr Lys Cys Ile Pro Ser Leu Glu Ala
 1               5                  10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Lys Cys Ile Pro Ser Leu Glu Ala Ala Val Lys
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Pro Ser Leu Glu Ala Ala Val Lys Gln Ala Tyr
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Glu Ala Ala Val Lys Gln Ala Tyr Ala Ala Thr
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Val Lys Gln Tyr Ala Ala Thr Tyr Ala Ala
 1               5                  10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ala Tyr Ala Ala Thr Val Ala Ala Ala Pro Gln
 1               5                  10
```

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Ala Ala Thr Val Ala Ala Ala Pro Gln Val Lys Tyr
 1               5                  10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Val Ala Ala Ala Pro Gln Val Lys Tyr Ala Val Phe
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ala Pro Gln Val Lys Tyr Ala Val Phe Glu Ala Ala
 1               5                  10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Val Lys Tyr Ala Val Phe Glu Ala Ala Leu Thr Lys
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Ala Val Phe Glu Ala Ala Leu Thr Lys Ala Ile Thr
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 72

Glu Ala Ala Leu Thr Lys Ala Ile Thr Ala Met Ser
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Thr Lys Ala Ile Thr Ala Met Ser Glu Val Gln
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ile Thr Ala Met Ser Glu Val Gln Lys Val Ser
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Met Ser Glu Val Gln Lys Val Ser Gln Pro Ala
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Val Gln Lys Val Ser Gln Pro Ala Thr Gly Ala
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Val Ser Gln Pro Ala Thr Gly Ala Ala Thr Val
 1               5                  10

<210> SEQ ID NO 78
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 78

Gln Pro Ala Thr Gly Ala Ala Thr Val Ala Ala Gly
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Gly Ala Ala Thr Val Ala Ala Gly Ala Ala Thr
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Thr Val Ala Ala Gly Ala Ala Thr Thr Ala Ala
 1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Ala Gly Ala Ala Thr Thr Ala Ala Gly Ala Ala
 1               5                  10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ala Thr Thr Ala Ala Gly Ala Ala Ser Gly Ala
 1               5                  10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ala Ala Gly Ala Ala Ser Gly Ala Ala Thr Val
 1               5                  10
```

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gly Ala Ala Ser Gly Ala Ala Thr Val Ala Ala Gly
 1               5                  10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ser Gly Ala Ala Thr Val Ala Ala Gly Gly Tyr Lys
 1               5                  10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Ala Ala Thr Val Ala Ala Gly Gly Tyr Lys Val
 1               5                  10

<210> SEQ ID NO 87
<211> LENGTH: 265
<212> TYPE: PRT
<213> ORGANISM: Artificial Sequence
<220> FEATURE:
<223> OTHER INFORMATION: Description of Artificial Sequence: Recombinant allergen

<400> SEQUENCE: 87

Ala Asp Ala Gly Tyr Ala Pro Ala Thr Pro Ala Ala Ala Gly Ala Ala
 1               5                  10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ser Val Pro Ala Ala
        35                  40                  45

Asp Lys Phe Lys Thr Phe Glu Ala Ala Phe Thr Ser Ser Lys Ala
    50                  55                  60

Ala Ala Lys Ala Pro Gly Leu Val Pro Lys Leu Asp Ala Ala Tyr
65                  70                  75                  80

Ser Val Ala Tyr Lys Ala Ala Val Gly Ala Thr Pro Glu Ala Lys Phe
                85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
        115                 120                 125

Ala Lys Ile Pro Ala Gly Glu Leu Gln Ile Ile Asp Lys Ile Asp Ala

```
                130                 135                 140
Ala Phe Lys Val Ala Ala Thr Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
                180                 185                 190

Ala Val Lys Gln Ala Tyr Ala Ala Thr Val Ala Ala Pro Gln Val
                195                 200                 205

Lys Tyr Ala Val Phe Glu Ala Ala Leu Thr Lys Ala Ile Thr Ala Met
    210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
                260                 265

<210> SEQ ID NO 88
<211> LENGTH: 265
<212> TYPE: PRT
<213> ORGANISM: Artificial Sequence
<220> FEATURE:
<223> OTHER INFORMATION: Description of Artificial Sequence: Recombinant
      allergen

<400> SEQUENCE: 88

Ala Asp Ala Gly Tyr Ala Pro Ala Thr Pro Ala Ala Ala Gly Ala Ala
  1               5                  10                  15

Ala Gly Lys Ala Thr Thr Glu Glu Gln Lys Leu Ile Glu Asp Ile Asp
                20                  25                  30

Val Gly Phe Lys Ala Ala Val Ala Ala Ala Ser Val Pro Ala Ala
                35                  40                  45

Leu Ala Phe Lys Thr Phe Glu Ala Ala Phe Thr Ser Ser Ser Lys Ala
    50                  55                  60

Ala Ala Ala Lys Ala Pro Gly Leu Val Pro Lys Leu Asp Ala Ala Tyr
 65                  70                  75                  80

Ser Val Ala Tyr Lys Ala Ala Val Gly Ala Thr Pro Glu Ala Lys Phe
                85                  90                  95

Asp Ser Phe Val Ala Ser Leu Thr Glu Ala Leu Arg Val Ile Ala Gly
                100                 105                 110

Ala Leu Glu Val His Ala Val Lys Pro Val Thr Glu Glu Pro Gly Met
    115                 120                 125

Ala Lys Ile Pro Ala Gly Glu Leu Gln Ile Ile Asp Lys Ile Asp Ala
    130                 135                 140

Ala Phe Lys Val Ala Ala Thr Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
                180                 185                 190

Ala Val Lys Gln Ala Tyr Ala Ala Thr Val Ala Ala Pro Gln Val
                195                 200                 205

Lys Tyr Ala Val Phe Glu Ala Ala Leu Thr Lys Ala Ile Thr Ala Met
    210                 215                 220
```

```
Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
                260             265

<210> SEQ ID NO 89
<211> LENGTH: 265
<212> TYPE: PRT
<213> ORGANISM: Artificial Sequence
<220> FEATURE:
<223> OTHER INFORMATION: Description of Artificial Sequence: Recombinant
      allergen

<400> SEQUENCE: 89

Ala Asp Ala Gly Tyr Ala Pro Ala Thr Pro Ala Ala Gly Ala Ala
 1               5                  10                  15

Ala Gly Lys Ala Thr Thr Glu Glu Gln Lys Leu Ile Glu Asp Ile Asn
                20                  25                  30

Val Gly Phe Lys Ala Ala Val Ala Ala Ala Ser Val Pro Ala Ala
                35                  40                  45

Leu Ala Phe Lys Thr Phe Glu Ala Ala Phe Thr Ser Ser Lys Ala
 50                  55                  60

Ala Ala Lys Ala Pro Gly Leu Val Pro Lys Leu Asp Ala Ala Tyr
 65                  70                  75                  80

Ser Val Ala Tyr Lys Ala Val Gly Ala Thr Pro Glu Ala Lys Phe
                85                  90                  95

Asp Ser Phe Val Ala Ser Leu Thr Glu Ala Leu Arg Val Ile Ala Gly
                100                 105                 110

Ala Leu Glu Val His Ala Val Lys Pro Val Thr Glu Glu Pro Gly Met
                115                 120                 125

Ala Lys Ile Pro Ala Gly Glu Leu Gln Ile Ile Asp Lys Ile Asp Ala
130                 135                 140

Ala Phe Lys Val Ala Ala Thr Ala Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
                180                 185                 190

Ala Val Lys Gln Ala Tyr Ala Ala Thr Val Ala Ala Pro Gln Val
                195                 200                 205

Lys Tyr Ala Val Phe Glu Ala Ala Leu Thr Lys Ala Ile Thr Ala Met
210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
                260             265

<210> SEQ ID NO 90
<211> LENGTH: 265
<212> TYPE: PRT
<213> ORGANISM: Artificial Sequence
<220> FEATURE:
<223> OTHER INFORMATION: Description of Artificial Sequence: Recombinant
      allergen
```

-continued

<400> SEQUENCE: 90

```
Ala Asp Ala Gly Tyr Ala Pro Ala Thr Pro Ala Ala Cys Gly Ala Ala
 1               5                  10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ser Val Pro Ala Ala
        35                  40                  45

Asp Lys Phe Lys Thr Phe Glu Ala Ala Phe Thr Ser Ser Lys Ala
    50                  55                  60

Ala Ala Ala Lys Ala Pro Gly Leu Val Pro Lys Leu Asp Ala Ala Tyr
65                  70                  75                  80

Ser Val Ala Tyr Lys Ala Val Gly Ala Thr Pro Glu Ala Lys Phe
                85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
        115                 120                 125

Ala Lys Ile Pro Ala Gly Glu Leu Gln Ile Ile Asp Lys Ile Asp Ala
    130                 135                 140

Ala Phe Lys Val Ala Ala Thr Ala Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Ala Pro Gln Val
        195                 200                 205

Lys Tyr Ala Val Phe Glu Ala Ala Leu Thr Lys Ala Ile Thr Ala Met
    210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
            260                 265
```

<210> SEQ ID NO 91
<211> LENGTH: 182
<212> TYPE: PRT
<213> ORGANISM: Artificial Sequence
<220> FEATURE:
<223> OTHER INFORMATION: Description of Artificial Sequence: Recombinant allergen

<400> SEQUENCE: 91

```
Ala Asp Ala Gly Tyr Ala Pro Ala Thr Pro Ala Ala Gly Ala Ala
 1               5                  10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ser Val Pro Ala Ala
        35                  40                  45

Leu Ala Gly Glu Leu Gln Ile Ile Asp Lys Ile Asp Ala Ala Phe Lys
    50                  55                  60

Val Ala Ala Thr Ala Ala Ala Thr Ala Pro Ala Asp Asp Lys Phe Thr
65                  70                  75                  80
```

```
Val Phe Glu Ala Ala Phe Asn Lys Ala Ile Lys Glu Ser Thr Gly Gly
                85                  90                  95

Ala Tyr Asp Thr Tyr Lys Cys Ile Pro Ser Leu Glu Ala Ala Val Lys
            100                 105                 110

Gln Ala Tyr Ala Ala Thr Val Ala Ala Pro Gln Val Lys Tyr Ala
        115                 120                 125

Val Phe Glu Ala Ala Leu Thr Lys Ala Ile Thr Ala Met Ser Glu Val
    130                 135                 140

Gln Lys Val Ser Gln Pro Ala Thr Gly Ala Ala Thr Val Ala Ala Gly
145                 150                 155                 160

Ala Ala Thr Thr Ala Gly Ala Ala Ser Gly Ala Ala Thr Val Ala
                165                 170                 175

Ala Gly Gly Tyr Lys Val
            180

<210> SEQ ID NO 92
<211> LENGTH: 137
<212> TYPE: PRT
<213> ORGANISM: Artificial Sequence
<220> FEATURE:
<223> OTHER INFORMATION: Description of Artificial Sequence: Recombinant
      allergen

<400> SEQUENCE: 92

Ala Asp Ala Gly Tyr Ala Pro Ala Thr Pro Ala Ala Gly Ala Ala
 1               5                  10                  15

Ala Gly Lys Ala Thr Thr Glu Glu Gln Lys Leu Ile Glu Asp Ile Asn
             20                  25                  30

Val Gly Phe Lys Ala Ala Val Ala Ala Ala Ser Val Pro Ala Ala
         35                  40                  45

Leu Ala Gly Ala Tyr Asp Thr Tyr Lys Cys Ile Pro Ser Leu Glu Ala
     50                  55                  60

Ala Val Lys Gln Ala Tyr Ala Ala Thr Val Ala Ala Pro Gln Val
 65                  70                  75                  80

Lys Tyr Ala Val Phe Glu Ala Ala Leu Thr Lys Ala Ile Thr Ala Met
                 85                  90                  95

Ser Glu Val Gln Lys Val Ser Gln Pro Ala Thr Gly Ala Ala Thr Val
            100                 105                 110

Ala Ala Gly Ala Ala Thr Thr Ala Gly Ala Ala Ser Gly Ala Ala
        115                 120                 125

Thr Val Ala Ala Gly Gly Tyr Lys Val
    130                 135

<210> SEQ ID NO 93
<211> LENGTH: 241
<212> TYPE: PRT
<213> ORGANISM: Artificial Sequence
<220> FEATURE:
<223> OTHER INFORMATION: Description of Artificial Sequence: Recombinant
      allergen

<400> SEQUENCE: 93

Ala Asp Ala Gly Tyr Ala Pro Ala Thr Pro Ala Ala Gly Ala Ala
 1               5                  10                  15

Ala Gly Lys Ala Thr Thr Glu Glu Gln Lys Leu Ile Glu Asp Ile Asn
             20                  25                  30

Val Gly Phe Lys Ala Ala Val Ala Ala Ala Ser Val Pro Ala Ala
         35                  40                  45
```

―continued

```
Asp Lys Phe Lys Thr Phe Glu Ala Ala Phe Thr Ser Ser Lys Ala
 50                  55                  60
Ala Ala Ala Lys Ala Pro Gly Leu Val Pro Lys Leu Asp Ala Ala Tyr
 65                  70                  75                  80
Ser Val Ala Tyr Lys Ala Ala Val Gly Ala Thr Pro Glu Ala Lys Phe
                 85                  90                  95
Asp Ser Phe Val Ala Ser Leu Thr Glu Ala Leu Arg Val Ile Ala Gly
            100                 105                 110
Ala Leu Glu Val His Ala Val Lys Pro Val Thr Glu Glu Pro Gly Met
        115                 120                 125
Ala Lys Ile Pro Ala Gly Glu Leu Gln Ile Ile Asp Lys Ile Asp Ala
    130                 135                 140
Ala Phe Lys Val Ala Ala Thr Ala Ala Gly Gly Ala Tyr Asp Thr Tyr
145                 150                 155                 160
Lys Cys Ile Pro Ser Leu Glu Ala Ala Val Lys Gln Ala Tyr Ala Ala
                165                 170                 175
Thr Val Ala Ala Ala Pro Gln Val Lys Tyr Ala Val Phe Glu Ala Ala
            180                 185                 190
Leu Thr Lys Thr Ile Thr Ala Met Ser Glu Val Gln Lys Val Ser Gln
        195                 200                 205
Pro Ala Thr Gly Ala Ala Thr Val Ala Ala Gly Ala Ala Thr Thr Ala
    210                 215                 220
Ala Gly Ala Ala Ser Gly Ala Ala Thr Val Ala Ala Gly Gly Tyr Lys
225                 230                 235                 240
Val
```

```
<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 94
atatggatcc atcgagggaa gggccgatgc cggctacgcc                           40

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 95
gaacgctagc gccgcaggga cgctggc                                        27

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 96
gcgctagcgt tcaagacctt cgag                                           24

<210> SEQ ID NO 97
<211> LENGTH: 31
<212> TYPE: DNA
```

-continued

```
<213> ORGANISM: Artificial Sequence
<220> FEATURE:
<223> OTHER INFORMATION: Description of Artificial Sequence: Primer

<400> SEQUENCE: 97
atataagctt tcctctgaag gaaggcaacc c                              31

<210> SEQ ID NO 98
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 98
atatggatcc atcgagggta gggccgatgc cggctacgcc ccggccaccc cggctgcatg     60
cggagcg                                                              67

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 99
gctagccggc gagctgcaga tcatcg                                         26
```